(12) United States Patent
Klein et al.

(10) Patent No.: US 12,419,862 B2
(45) Date of Patent: Sep. 23, 2025

(54) USE OF A CATHEPSIN S INHIBITOR AGAINST THE FORMATION OF ANTI-DRUG ANTIBODIES

(71) Applicant: Hoffmann-La Roche Inc., Little Falls, NJ (US)

(72) Inventors: Christian Klein, Schlieren (CH); Fabrice Alain Andre Kolb, Basel (CH); Marianne Manchester Young, Basel (CH); Syed Sohail Ahmed, Basel (CH); Juliana Mattos De Almeida Bessa, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 927 days.

(21) Appl. No.: 17/206,044

(22) Filed: Mar. 18, 2021

(65) Prior Publication Data
US 2021/0315863 A1  Oct. 14, 2021

Related U.S. Application Data

(63) Continuation of application No. PCT/EP2019/074918, filed on Sep. 18, 2019.

(30) Foreign Application Priority Data

Sep. 18, 2018 (EP) .................................... 18195251

(51) Int. Cl.
*A61K 31/4155* (2006.01)
*A61P 37/06* (2006.01)
*C07K 16/24* (2006.01)

(52) U.S. Cl.
CPC .......... *A61K 31/4155* (2013.01); *A61P 37/06* (2018.01); *C07K 16/241* (2013.01)

(58) Field of Classification Search
CPC ............ A61K 31/4155; A61K 31/4025; A61K 45/06; A61K 2300/00; A61K 31/41; A61K 39/395; A61K 2039/505; A61K 2039/545; A61P 37/06; C07K 16/241
See application file for complete search history.

(56) References Cited

U.S. PATENT DOCUMENTS

| | | | |
|---|---|---|---|
| 2007/0141059 A1* | 6/2007 | Elrod | A61P 37/00 514/56 |
| 2009/0269360 A1 | 10/2009 | Olwill et al. | |
| 2010/0267722 A1 | 10/2010 | Sanchez et al. | |
| 2013/0217665 A1 | 8/2013 | Banner et al. | |
| 2017/0209573 A1 | 7/2017 | Bacac et al. | |
| 2018/0135012 A1 | 5/2018 | Mata-Fink et al. | |

FOREIGN PATENT DOCUMENTS

| | | | |
|---|---|---|---|
| JP | 2009-533404 A | 9/2009 | |
| JP | 2012-524166 A | 10/2012 | |
| TW | 201040164 A1 | 11/2010 | |
| WO | 2010/094981 A2 | 8/2010 | |
| WO | WO-2010121918 A1 * | 10/2010 | .............. A61P 11/00 |
| WO | WO-2013068434 A1 * | 5/2013 | ................ A61P 3/10 |
| WO | WO-2016034602 A1 * | 3/2016 | ........... C07D 403/12 |
| WO | 2017/096262 A1 | 6/2017 | |
| WO | 2017/144483 A1 | 8/2017 | |

OTHER PUBLICATIONS

Andrick et al. Predicting Hemagglutinin MHC-II Ligand Analogues in Anti-TNFa Biologics: Implications for Immunogenicity of Pharmaceutical Proteins (PLoS ONE, 10(8), p. 1-21). (Year: 2015).*
Belikov, V.G. "Pharmaceutical Chemistry," Tutorial, 4th, revised and expanded edition, Moscow, MEDPress-Inform, 2007, pp. 27-29 (including English Translation).
Boyang et al., "Biotechnology of Traditional Chinese Medicine" 397:1-4 (2005).
International Preliminary Report on Patentability for PCT/EP2019/074918 completed on Aug. 21, 2020.
International Search Report for PCT/EP2019/074918 mailed Dec. 19, 2019.
Krishna, M. et al., "Immunogenicity to Biotherapeutics—The Role of Anti-drug Immune Complexes" Front. Immunol. 7(Article 21):1-13 (2016).
Mashkowsky, M.D. et al., "Medicine" (ISBN 978-5-7864-0218-7),:1-4 (2012).
Selezneva, A. I., et al., "Complex Approach to Study Pharmacological Agents In Vitro, Ex Vivo, In Vivo" International Scientific Research Journal 6(37):125-127 (2015).
Theron, M., et al., "Pharmacodynamic Monitoring of RO5459072, a small Molecule Inhibitor of Cathepsin S" Frontiers in Immunology 8(Article 806):1-14 (2017).
Thurmond, R. L., et al., "Cathepsin S inhibitors as novel immunomodulators" Curr. Opin. Investig. Drugs 6(5):473-482 (2005).

* cited by examiner

*Primary Examiner* — Joseph K McKane
*Assistant Examiner* — Meghan C Heasley
(74) *Attorney, Agent, or Firm* — Bradley E. Davis

(57) ABSTRACT

The present invention relates in particular to a cathepsin S inhibitor for use in a method for reducing or preventing the formation of anti-drug antibodies (ADA) against a therapeutic agent in a subject who is receiving a treatment with said therapeutic agent.

Figure 1:
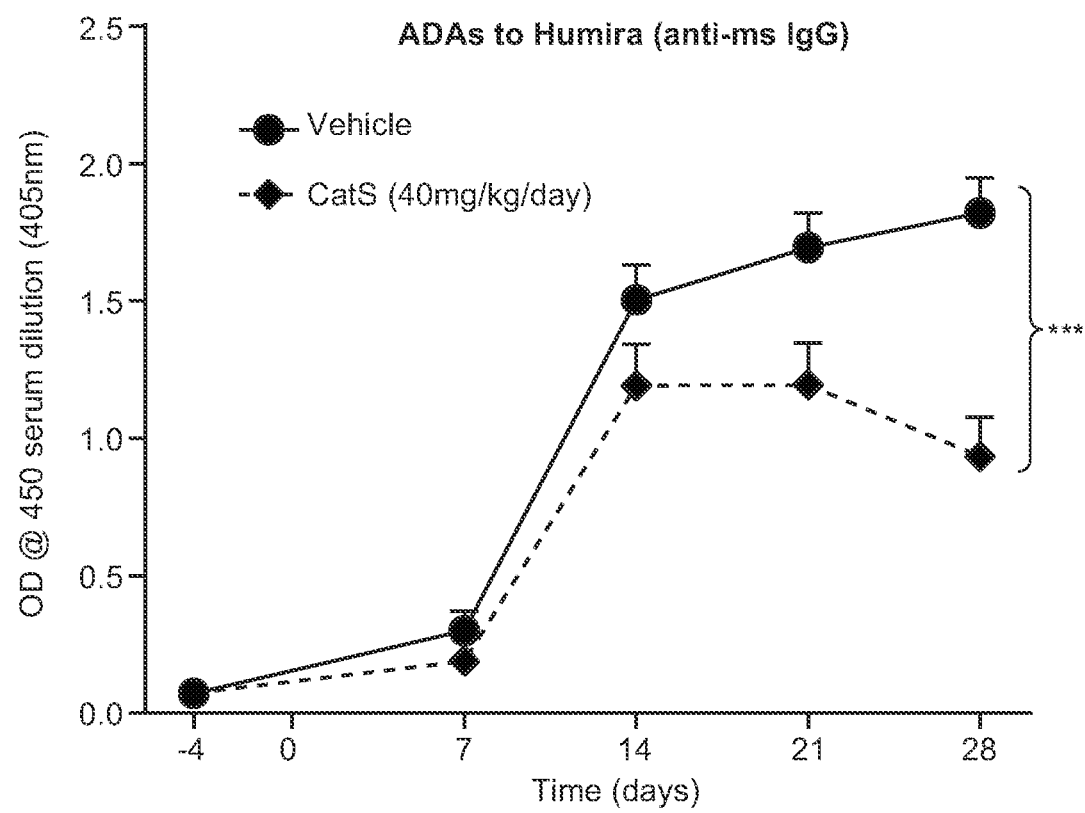

23 Claims, 12 Drawing Sheets
Specification includes a Sequence Listing.

SEQUENCE LISTING

<160> NUMBER OF SEQ ID NOS: 6

<210> SEQ ID NO 1
<211> LENGTH: 816
<212> TYPE: PRT
<213> ORGANISM: Artificial Sequence
<220> FEATURE:
<223> OTHER INFORMATION: Synthetic construct

<400> SEQUENCE: 1

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Val Glu Pro Lys Ser Cys Asp Gly Gly
210                 215                 220

Gly Gly Ser Gly Gly Gly Ser Gln Val Gln Leu Val Gln Ser Gly
225                 230                 235                 240

Ala Glu Val Lys Lys Pro Gly Ser Ser Val Lys Val Ser Cys Lys Ala
                245                 250                 255

Ser Gly Gly Thr Phe Ser Ser Tyr Ala Ile Ser Trp Val Arg Gln Ala
            260                 265                 270

Pro Gly Gln Gly Leu Glu Trp Met Gly Gly Ile Ile Pro Ile Phe Gly
        275                 280                 285

Thr Ala Asn Tyr Ala Gln Lys Phe Gln Gly Arg Val Thr Ile Thr Ala
290                 295                 300

Asp Lys Ser Thr Ser Thr Ala Tyr Met Glu Leu Ser Ser Leu Arg Ser
305                 310                 315                 320

Glu Asp Thr Ala Val Tyr Tyr Cys Ala Arg Glu Tyr Tyr Arg Gly Pro
                325                 330                 335

Tyr Asp Tyr Trp Gly Gln Gly Thr Thr Val Thr Val Ser Ser Ala Ser
            340                 345                 350

Thr Lys Gly Pro Ser Val Phe Pro Leu Ala Pro Ser Ser Lys Ser Thr
        355                 360                 365

Ser Gly Gly Thr Ala Ala Leu Gly Cys Leu Val Lys Asp Tyr Phe Pro
370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415
```

-continued

Ser Val Val Thr Val Pro Ser Ser Leu Gly Thr Gln Thr Tyr Ile
              420              425              430

Cys Asn Val Asn His Lys Pro Ser Asn Thr Lys Val Asp Lys Lys Val
              435              440              445

Glu Pro Lys Ser Cys Asp Lys Thr His Thr Cys Pro Pro Cys Pro Ala
450              455              460

Pro Glu Ala Ala Gly Gly Pro Ser Val Phe Leu Phe Pro Pro Lys Pro
465              470              475              480

Lys Asp Thr Leu Met Ile Ser Arg Thr Pro Glu Val Thr Cys Val Val
              485              490              495

Val Asp Val Ser His Glu Asp Pro Glu Val Lys Phe Asn Trp Tyr Val
              500              505              510

Asp Gly Val Glu Val His Asn Ala Lys Thr Lys Pro Arg Glu Glu Gln
              515              520              525

Tyr Asn Ser Thr Tyr Arg Val Val Ser Val Leu Thr Val Leu His Gln
              530              535              540

Asp Trp Leu Asn Gly Lys Glu Tyr Lys Cys Lys Val Ser Asn Lys Ala
545              550              555              560

Leu Gly Ala Pro Ile Glu Lys Thr Ile Ser Lys Ala Lys Gly Gln Pro
              565              570              575

Arg Glu Pro Gln Val Tyr Thr Leu Pro Pro Cys Arg Asp Glu Leu Thr
              580              585              590

Lys Asn Gln Val Ser Leu Trp Cys Leu Val Lys Gly Phe Tyr Pro Ser
              595              600              605

Asp Ile Ala Val Glu Trp Glu Ser Asn Gly Gln Pro Glu Asn Asn Tyr
              610              615              620

Lys Thr Thr Pro Pro Val Leu Asp Ser Asp Gly Ser Phe Phe Leu Tyr
625              630              635              640

Ser Lys Leu Thr Val Asp Lys Ser Arg Trp Gln Gln Gly Asn Val Phe
              645              650              655

Ser Cys Ser Val Met His Glu Ala Leu His Asn His Tyr Thr Gln Lys
              660              665              670

Ser Leu Ser Leu Ser Pro Gly Gly Gly Gly Ser Gly Gly Gly Gly
              675              680              685

Ser Gly Gly Gly Gly Ser Gly Gly Gly Gly Ser Glu Val Gln Leu Leu
              690              695              700

Glu Ser Gly Gly Gly Leu Val Gln Pro Gly Gly Ser Leu Arg Leu Ser
705              710              715              720

Cys Ala Ala Ser Gly Phe Thr Phe Ser Ser Tyr Ala Met Ser Trp Val
              725              730              735

Arg Gln Ala Pro Gly Lys Gly Leu Glu Trp Val Ser Ala Ile Ile Gly
              740              745              750

Ser Gly Ala Ser Thr Tyr Tyr Ala Asp Ser Val Lys Gly Arg Phe Thr
              755              760              765

Ile Ser Arg Asp Asn Ser Lys Asn Thr Leu Tyr Leu Gln Met Asn Ser
              770              775              780

Leu Arg Ala Glu Asp Thr Ala Val Tyr Tyr Cys Ala Lys Gly Trp Phe
785              790              795              800

Gly Gly Phe Asn Tyr Trp Gly Gln Gly Thr Leu Val Thr Val Ser Ser
              805              810              815

<210> SEQ ID NO 2
<211> LENGTH: 807

```
<212> TYPE: PRT
<213> ORGANISM: Artificial Sequence
<220> FEATURE:
<223> OTHER INFORMATION: Synthetic construct

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Gly Gly
    210                 215                 220

Gly Gly Ser Gly Gly Gly Ser Gln Val Gln Leu Val Gln Ser Gly
225                 230                 235                 240

Ala Glu Val Lys Lys Pro Gly Ser Ser Val Lys Val Ser Cys Lys Ala
                245                 250                 255

Ser Gly Gly Thr Phe Ser Ser Tyr Ala Ile Ser Trp Val Arg Gln Ala
            260                 265                 270

Pro Gly Gln Gly Leu Glu Trp Met Gly Gly Ile Ile Pro Ile Phe Gly
        275                 280                 285

Thr Ala Asn Tyr Ala Gln Lys Phe Gln Gly Arg Val Thr Ile Thr Ala
    290                 295                 300

Asp Lys Ser Thr Ser Thr Ala Tyr Met Glu Leu Ser Ser Leu Arg Ser
305                 310                 315                 320

Glu Asp Thr Ala Val Tyr Tyr Cys Ala Arg Glu Tyr Tyr Arg Gly Pro
                325                 330                 335

Tyr Asp Tyr Trp Gly Gln Gly Thr Thr Val Thr Val Ser Ser Ala Ser
            340                 345                 350

Thr Lys Gly Pro Ser Val Phe Pro Leu Ala Pro Ser Ser Lys Ser Thr
        355                 360                 365

Ser Gly Gly Thr Ala Ala Leu Gly Cys Leu Val Lys Asp Tyr Phe Pro
    370                 375                 380
```

```
Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
            405                 410                 415

Ser Val Val Thr Val Pro Ser Ser Ser Leu Gly Thr Gln Thr Tyr Ile
            420                 425                 430

Cys Asn Val Asn His Lys Pro Ser Asn Thr Lys Val Asp Lys Lys Val
            435                 440                 445

Glu Pro Lys Ser Cys Asp Lys Thr His Thr Cys Pro Pro Cys Pro Ala
450                 455                 460

Pro Glu Ala Ala Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
            485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
            515                 520                 525

Tyr Asn Ser Thr Tyr Arg Val Val Ser Val Leu Thr Val Leu His Gln
530                 535                 540

Asp Trp Leu Asn Gly Lys Glu Tyr Lys Cys Lys Val Ser Asn Lys Ala
545                 550                 555                 560

Leu Gly Ala Pro Ile Glu Lys Thr Ile Ser Lys Ala Lys Gly Gln Pro
            565                 570                 575

Arg Glu Pro Gln Val Cys Thr Leu Pro Pro Ser Arg Asp Glu Leu Thr
            580                 585                 590

Lys Asn Gln Val Ser Leu Ser Cys Ala Val Lys Gly Phe Tyr Pro Ser
            595                 600                 605

Asp Ile Ala Val Glu Trp Glu Ser Asn Gly Gln Pro Glu Asn Asn Tyr
            610                 615                 620

Lys Thr Thr Pro Pro Val Leu Asp Ser Asp Gly Ser Phe Phe Leu Val
625                 630                 635                 640

Ser Lys Leu Thr Val Asp Lys Ser Arg Trp Gln Gln Gly Asn Val Phe
            645                 650                 655

Ser Cys Ser Val Met His Glu Ala Leu His Asn His Tyr Thr Gln Lys
            660                 665                 670

Ser Leu Ser Leu Ser Pro Gly Gly Gly Gly Ser Gly Gly Gly Gly
            675                 680                 685

Ser Gly Gly Gly Gly Ser Gly Gly Gly Gly Ser Glu Ile Val Leu Thr
690                 695                 700

Gln Ser Pro Gly Thr Leu Ser Leu Ser Pro Gly Glu Arg Ala Thr Leu
705                 710                 715                 720

Ser Cys Arg Ala Ser Gln Ser Val Thr Ser Ser Tyr Leu Ala Trp Tyr
            725                 730                 735

Gln Gln Lys Pro Gly Gln Ala Pro Arg Leu Leu Ile Asn Val Gly Ser
            740                 745                 750

Arg Arg Ala Thr Gly Ile Pro Asp Arg Phe Ser Gly Ser Gly Ser Gly
            755                 760                 765

Thr Asp Phe Thr Leu Thr Ile Ser Arg Leu Glu Pro Glu Asp Phe Ala
            770                 775                 780

Val Tyr Tyr Cys Gln Gln Gly Ile Met Leu Pro Pro Thr Phe Gly Gln
785                 790                 795                 800

Gly Thr Lys Val Glu Ile Lys
```

```
<210> SEQ ID NO 3
<211> LENGTH: 214
<212> TYPE: PRT
<213> ORGANISM: Artificial Sequence
<220> FEATURE:
<223> OTHER INFORMATION: Synthetic construct

<400> SEQUENCE: 3

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 805
<212> TYPE: PRT
<213> ORGANISM: Artificial Sequence
<220> FEATURE:
<223> OTHER INFORMATION: Synthetic construct

<400> SEQUENCE: 4

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Gly Tyr
            20                  25                  30

Asn Leu His Trp Val Arg Gln Pro Pro Gly Lys Gly Leu Glu Trp Met
        35                  40                  45

Gly Arg Met Arg Tyr Asp Gly Asp Thr Tyr Tyr Asn Ser Val Leu Lys
50                  55                  60

Ser Arg Leu Ser Ile Ser Arg Asp Thr Ser Lys Asn Gln Val Phe Leu
65                  70                  75                  80
```

-continued

Lys Met Asn Ser Leu Gln Thr Asp Asp Thr Ala Ile Tyr Tyr Cys Thr
            85                  90                  95

Arg Asp Gly Arg Gly Asp Ser Phe Asp Tyr Trp Gly Gln Gly Val Met
            100                 105                 110

Val Thr Val Ser Ser Ala Lys Thr Thr Pro Pro Ser Val Tyr Pro Leu
            115                 120                 125

Ala Pro Gly Ser Ala Ala Gln Thr Asn Ser Met Val Thr Leu Gly Cys
            130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                    165                 170                 175

Asp Leu Tyr Thr Leu Ser Ser Ser Val Thr Val Pro Ser Ser Thr Trp
                180                 185                 190

Pro Ser Gln Thr Val Thr Cys Asn Val Ala His Pro Ala Ser Ser Thr
            195                 200                 205

Lys Val Asp Lys Lys Ile Val Pro Arg Asp Cys Gly Gly Gly Gly Ser
            210                 215                 220

Gly Gly Gly Gly Ser Gln Val Gln Leu Lys Glu Ser Gly Pro Gly Leu
225                 230                 235                 240

Val Gln Pro Ser Gln Thr Leu Ser Leu Thr Cys Thr Val Ser Gly Phe
                245                 250                 255

Ser Leu Thr Gly Tyr Asn Leu His Trp Val Arg Gln Pro Pro Gly Lys
                260                 265                 270

Gly Leu Glu Trp Met Gly Arg Met Arg Tyr Asp Gly Asp Thr Tyr Tyr
                275                 280                 285

Asn Ser Val Leu Lys Ser Arg Leu Ser Ile Ser Arg Asp Thr Ser Lys
            290                 295                 300

Asn Gln Val Phe Leu Lys Met Asn Ser Leu Gln Thr Asp Asp Thr Ala
305                 310                 315                 320

Ile Tyr Tyr Cys Thr Arg Asp Gly Arg Gly Asp Ser Phe Asp Tyr Trp
                325                 330                 335

Gly Gln Gly Val Met Val Thr Val Ser Ser Ala Lys Thr Thr Pro Pro
                340                 345                 350

Ser Val Tyr Pro Leu Ala Pro Gly Ser Ala Ala Gln Thr Asn Ser Met
            355                 360                 365

Val Thr Leu Gly Cys Leu Val Lys Gly Tyr Phe Pro Glu Pro Val Thr
            370                 375                 380

Val Thr Trp Asn Ser Gly Ser Leu Ser Ser Gly Val His Thr Phe Pro
385                 390                 395                 400

Ala Val Leu Gln Ser Asp Leu Tyr Thr Leu Ser Ser Ser Val Thr Val
                405                 410                 415

Pro Ser Ser Thr Trp Pro Ser Gln Thr Val Thr Cys Asn Val Ala His
            420                 425                 430

Pro Ala Ser Ser Thr Lys Val Asp Lys Lys Ile Val Pro Arg Asp Cys
            435                 440                 445

Gly Cys Lys Pro Cys Ile Cys Thr Val Pro Glu Val Ser Ser Val Phe
            450                 455                 460

Ile Phe Pro Pro Lys Pro Lys Asp Val Leu Thr Ile Thr Leu Thr Pro
465                 470                 475                 480

Lys Val Thr Cys Val Val Val Ala Ile Ser Lys Asp Asp Pro Glu Val
                485                 490                 495

Gln Phe Ser Trp Phe Val Asp Asp Val Glu Val His Thr Ala Gln Thr

```
                500               505               510
Lys Pro Arg Glu Glu Gln Ile Asn Ser Thr Phe Arg Ser Val Ser Glu
            515                 520                 525

Leu Pro Ile Met His Gln Asp Trp Leu Asn Gly Lys Glu Phe Lys Cys
            530                 535             540

Arg Val Asn Ser Ala Ala Phe Gly Ala Pro Ile Glu Lys Thr Ile Ser
545                 550                 555                 560

Lys Thr Lys Gly Arg Pro Lys Ala Pro Gln Val Tyr Thr Ile Pro Pro
                565                 570                 575

Pro Lys Lys Gln Met Ala Lys Asp Lys Val Ser Leu Thr Cys Met Ile
            580                 585                 590

Thr Asn Phe Phe Pro Glu Asp Ile Thr Val Glu Trp Gln Trp Asn Gly
            595                 600                 605

Gln Pro Ala Glu Asn Tyr Lys Asn Thr Gln Pro Ile Met Lys Thr Asp
            610                 615                 620

Gly Ser Tyr Phe Val Tyr Ser Lys Leu Asn Val Gln Lys Ser Asn Trp
625                 630                 635                 640

Glu Ala Gly Asn Thr Phe Thr Cys Ser Val Leu His Glu Gly Leu His
                645                 650                 655

Asn His His Thr Glu Lys Ser Leu Ser His Ser Pro Gly Gly Gly Gly
            660                 665                 670

Gly Ser Gly Gly Gly Ser Gly Gly Gly Ser Gly Gly Gly Gly
            675                 680                 685

Ser Glu Val Gln Leu Leu Glu Ser Gly Gly Leu Val Gln Pro Gly
            690                 695                 700

Gly Ser Leu Arg Leu Ser Cys Ala Ala Ser Gly Phe Thr Phe Ser Ser
705                 710                 715                 720

His Ala Met Ser Trp Val Arg Gln Ala Pro Gly Lys Gly Leu Glu Trp
                725                 730                 735

Val Ser Ala Ile Trp Ala Ser Gly Glu Gln Tyr Tyr Ala Asp Ser Val
                740                 745                 750

Lys Gly Arg Phe Thr Ile Ser Arg Asp Asn Ser Lys Asn Thr Leu Tyr
            755                 760                 765

Leu Gln Met Asn Ser Leu Arg Ala Glu Asp Thr Ala Val Tyr Tyr Cys
            770                 775                 780

Ala Lys Gly Trp Leu Gly Asn Phe Asp Tyr Trp Gly Gln Gly Thr Leu
785                 790                 795                 800

Val Thr Val Ser Ser
                805

<210> SEQ ID NO 5
<211> LENGTH: 797
<212> TYPE: PRT
<213> ORGANISM: Artificial Sequence
<220> FEATURE:
<223> OTHER INFORMATION: Synthetic construct

<400> SEQUENCE: 5

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Gly Tyr
                20                  25                  30

Asn Leu His Trp Val Arg Gln Pro Pro Gly Lys Gly Leu Glu Trp Met
            35                  40                  45

Gly Arg Met Arg Tyr Asp Gly Asp Thr Tyr Tyr Asn Ser Val Leu Lys
```

```
                50                  55                  60
Ser Arg Leu Ser Ile Ser Arg Asp Thr Ser Lys Asn Gln Val Phe Leu
 65                  70                  75                  80

Lys Met Asn Ser Leu Gln Thr Asp Asp Thr Ala Ile Tyr Tyr Cys Thr
                 85                  90                  95

Arg Asp Gly Arg Gly Asp Ser Phe Asp Tyr Trp Gly Gln Gly Val Met
                100                 105                 110

Val Thr Val Ser Ser Ala Lys Thr Thr Pro Pro Ser Val Tyr Pro Leu
                115                 120                 125

Ala Pro Gly Ser Ala Ala Gln Thr Asn Ser Met Val Thr Leu Gly Cys
130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
                180                 185                 190

Pro Ser Gln Thr Val Thr Cys Asn Val Ala His Pro Ala Ser Ser Thr
                195                 200                 205

Lys Val Asp Lys Lys Ile Val Pro Arg Asp Cys Gly Gly Gly Gly Ser
210                 215                 220

Gly Gly Gly Gly Ser Gln Val Gln Leu Lys Glu Ser Gly Pro Gly Leu
225                 230                 235                 240

Val Gln Pro Ser Gln Thr Leu Ser Leu Thr Cys Thr Val Ser Gly Phe
                245                 250                 255

Ser Leu Thr Gly Tyr Asn Leu His Trp Val Arg Gln Pro Pro Gly Lys
                260                 265                 270

Gly Leu Glu Trp Met Gly Arg Met Arg Tyr Asp Gly Asp Thr Tyr Tyr
                275                 280                 285

Asn Ser Val Leu Lys Ser Arg Leu Ser Ile Ser Arg Asp Thr Ser Lys
290                 295                 300

Asn Gln Val Phe Leu Lys Met Asn Ser Leu Gln Thr Asp Asp Thr Ala
305                 310                 315                 320

Ile Tyr Tyr Cys Thr Arg Asp Gly Arg Gly Asp Ser Phe Asp Tyr Trp
                325                 330                 335

Gly Gln Gly Val Met Val Thr Val Ser Ser Ala Lys Thr Thr Pro Pro
                340                 345                 350

Ser Val Tyr Pro Leu Ala Pro Gly Ser Ala Ala Gln Thr Asn Ser Met
                355                 360                 365

Val Thr Leu Gly Cys Leu Val Lys Gly Tyr Phe Pro Glu Pro Val Thr
                370                 375                 380

Val Thr Trp Asn Ser Gly Ser Leu Ser Ser Gly Val His Thr Phe Pro
385                 390                 395                 400

Ala Val Leu Gln Ser Asp Leu Tyr Thr Leu Ser Ser Ser Val Thr Val
                405                 410                 415

Pro Ser Ser Thr Trp Pro Ser Gln Thr Val Thr Cys Asn Val Ala His
                420                 425                 430

Pro Ala Ser Ser Thr Lys Val Asp Lys Lys Ile Val Pro Arg Asp Cys
                435                 440                 445

Gly Cys Lys Pro Cys Ile Cys Thr Val Pro Glu Val Ser Ser Val Phe
                450                 455                 460

Ile Phe Pro Pro Lys Pro Lys Asp Val Leu Thr Ile Thr Leu Thr Pro
465                 470                 475                 480
```

```
Lys Val Thr Cys Val Val Ala Ile Ser Lys Asp Pro Glu Val
                485                 490                 495

Gln Phe Ser Trp Phe Val Asp Asp Val Glu Val His Thr Ala Gln Thr
            500                 505                 510

Lys Pro Arg Glu Glu Gln Ile Asn Ser Thr Phe Arg Ser Val Ser Glu
        515                 520                 525

Leu Pro Ile Met His Gln Asp Trp Leu Asn Gly Lys Glu Phe Lys Cys
    530                 535                 540

Arg Val Asn Ser Ala Ala Phe Gly Ala Pro Ile Glu Lys Thr Ile Ser
545                 550                 555                 560

Lys Thr Lys Gly Arg Pro Lys Ala Pro Gln Val Tyr Thr Ile Pro Pro
                565                 570                 575

Pro Lys Glu Gln Met Ala Lys Asp Lys Val Ser Leu Thr Cys Met Ile
            580                 585                 590

Thr Asn Phe Phe Pro Glu Asp Ile Thr Val Glu Trp Gln Trp Asn Gly
        595                 600                 605

Gln Pro Ala Glu Asn Tyr Asp Asn Thr Gln Pro Ile Met Asp Thr Asp
    610                 615                 620

Gly Ser Tyr Phe Val Tyr Ser Asp Leu Asn Val Gln Lys Ser Asn Trp
625                 630                 635                 640

Glu Ala Gly Asn Thr Phe Thr Cys Ser Val Leu His Glu Gly Leu His
                645                 650                 655

Asn His His Thr Glu Lys Ser Leu Ser His Ser Pro Gly Gly Gly Gly
            660                 665                 670

Gly Ser Gly Gly Gly Ser Gly Gly Gly Ser Gly Gly Gly Gly
        675                 680                 685

Ser Glu Ile Val Leu Thr Gln Ser Pro Gly Thr Leu Ser Leu Ser Pro
    690                 695                 700

Gly Glu Arg Ala Thr Leu Ser Cys Arg Ala Ser Gln Ser Val Ser Arg
705                 710                 715                 720

Ser Tyr Leu Ala Trp Tyr Gln Gln Lys Pro Gly Gln Ala Pro Arg Leu
                725                 730                 735

Leu Ile Ile Gly Ala Ser Thr Arg Ala Thr Gly Ile Pro Asp Arg Phe
            740                 745                 750

Ser Gly Ser Gly Ser Gly Thr Asp Phe Thr Leu Thr Ile Ser Arg Leu
        755                 760                 765

Glu Pro Glu Asp Phe Ala Val Tyr Tyr Cys Gln Gln Gly Gln Val Ile
    770                 775                 780

Pro Pro Thr Phe Gly Gln Gly Thr Lys Val Glu Ile Lys
785                 790                 795

<210> SEQ ID NO 6
<211> LENGTH: 219
<212> TYPE: PRT
<213> ORGANISM: Artificial Sequence
<220> FEATURE:
<223> OTHER INFORMATION: Synthetic construct

<400> SEQUENCE: 6

Asp Ile Val Met Thr Gln Gly Ala Leu Pro Asn Pro Val Ser Gly
1               5                   10                  15

Glu Ser Ala Ser Ile Thr Cys Arg Ser Ser Gln Ser Leu Val Tyr Lys
            20                  25                  30

Asp Gly Gln Thr Tyr Leu Asn Trp Phe Leu Gln Arg Pro Gly Gln Ser
        35                  40                  45
```

-continued

```
Pro Gln Leu Leu Thr Tyr Trp Met Ser Thr Arg Ala Ser Gly Val Ser
    50              55              60

Asp Arg Phe Ser Gly Ser Gly Ser Gly Thr Tyr Phe Thr Leu Lys Ile
65          70              75                      80

Ser Arg Val Arg Ala Glu Asp Ala Gly Val Tyr Tyr Cys Gln Gln Val
            85              90                  95

Arg Glu Tyr Pro Phe Thr Phe Gly Ser Gly Thr Lys Leu Glu Ile Lys
            100             105                 110

Arg Ala Asp Ala Ala Pro Thr Val Ser Ile Phe Pro Pro Ser Ser Glu
        115             120             125

Gln Leu Thr Ser Gly Gly Ala Ser Val Val Cys Phe Leu Asn Asn Phe
    130             135             140

Tyr Pro Lys Asp Ile Asn Val Lys Trp Lys Ile Asp Gly Ser Glu Arg
145             150             155                 160

Gln Asn Gly Val Leu Asn Ser Trp Thr Asp Gln Asp Ser Lys Asp Ser
                165             170             175

Thr Tyr Ser Met Ser Ser Thr Leu Thr Leu Thr Lys Asp Glu Tyr Glu
            180             185                 190

Arg His Asn Ser Tyr Thr Cys Glu Ala Thr His Lys Thr Ser Thr Ser
        195             200             205

Pro Ile Val Lys Ser Phe Asn Arg Asn Glu Cys
210             215
```

USE OF A CATHEPSIN S INHIBITOR AGAINST THE FORMATION OF ANTI-DRUG ANTIBODIES

CROSS-REFERENCE TO RELATED APPLICATIONS

This application is a continuation of International Application No. PCT/EP2019/074918 having an International filing date of Sep. 18, 2019 which claims priority to European Patent Application No. 18195251.6 filed on Sep. 18, 2018, both of which are incorporated herein in their entirety.

SEQUENCE LISTING

The instant application contains a Sequence Listing which has been submitted electronically in ASCII format and is hereby incorporated by reference in its entirety. Said ASCII copy, created on Mar. 18, 2021, is named P35022-US_Sequence_Listing.txt and is 32,142 bytes in size.

FIELD OF INVENTION

The present invention is directed in particular to a cathepsin S inhibitor for use in a method for reducing or preventing the formation of anti-drug antibodies (ADA) against a therapeutic agent in a subject who is receiving a treatment with said therapeutic agent.

Protein-based biologics, namely Immunomodulatory drugs, are effective therapeutic agents and their clinical applications have significantly grown during the past years due to its high specificity to immune targets (Leader, Baca et al., Nat Rev Drug Discov 2008, 7(1): 21-39). However, along with its superior efficacy and safety profile compared with small-molecules, some adverse reactions, including immunogenicity, are often reported (Sathish, Sethu et al., Nat Rev Drug Discov 2013, 12(4): 306-324; Boehncke and Brembilla, Expert Rev Clin Immunol 2018, 14(6): 513-523). Immunogenicity is characterized by anti-drug-antibody (ADA) formation which can be innocuous but can also lead to loss or reduced efficacy, altered pharmacokinetics, infusion reactions, crossreactivity to endogenous protein and in severe cases to anaphylactic reactions (Abramowicz, Crusiaux et al., N Engl J Med 1992, 327(10): 736, Baudouin, Crusiaux et al., Transplantation 2003, 76(3): 459-463). These unwanted effects are often the reason for therapy discontinuation and hence explain the urgent need for strategies aimed to mitigate ADA in the clinic. For this purpose, B-cell depleting agents, like Gazyva, have been applied in the clinic in combination with cancer immunotherapy (CIT) treatments and showed to supress de novo ADA responses. However, the complete ablation of B-cells may be undesired to patients as the role of B-cells in the mode of action of CITs is not completely known.

Mammalian cathepsins are cysteine-type proteases involved in key steps of biological and pathological events. Cathepsins are considered tractable drug targets as it is feasible to inhibit enzymatic activity with small molecules and are therefore of interest to the pharmaceutical industry (Bromme, D. (2001), 'Papain-like cysteine proteases', Curr Protoc Protein Sci, Chapter 21, Unit 21 2; Roberts, R. (2005), 'Lysosomal cysteine proteases: structure, function and inhibition of cathepsins', Drug News Perspect, 18 (10), 605-14).

Cathepsin S is prominently expressed in antigen presenting cells like macrophages and dendritic cells and smooth muscle cells. (Hsing, L. C. and Rudensky, A. Y. (2005), 'The lysosomal cysteine proteases in MHC class II antigen presentation', Immunol Rev, 207, 229-41; Rudensky, A. and Beers, C. (2006), 'Lysosomal cysteine proteases and antigen presentation', Ernst Schering Res Found Workshop, (56), 81-95). While Cathepsin S is only weakly expressed in normal arterial tissue, strong upregulation is seen in atherosclerotic arteries (Liu, J., et al. (2006), 'Increased serum cathepsin S in patients with atherosclerosis and diabetes', Atherosclerosis, 186 (2), 411-9; Sukhova, G. K., et al. (1998), 'Expression of the elastolytic cathepsins S and K in human atheroma and regulation of their production in smooth muscle cells', J Clin Invest, 102 (3), 576-83).

Preclinical data suggest that the function of Cathepsin S is critical for atherosclerosis as Cathepsin S deficient mice have a reduced atherosclerosis-phenotype when tested in appropriate mouse models. In LDL-Rec deficient mice reduced lipid accumulation, elastin-fibre breakdown and chronic arterial inflammation is reported. In APO E deficient mice, a significant reduction of acute plaque rupture events was reported. When chronic renal disease is introduced into CatS/In APO-E deficient mice a strong reduction of accelerated calcification is seen on top of the anti atherosclerotic activity in arteries and heart valves (Aikawa, E., et al. (2009), 'Arterial and aortic valve calcification abolished by elastolytic cathepsin S deficiency in chronic renal disease', Circulation, 119 (13), 1785-94; de Nooijer, R., et al. (2009), 'Leukocyte cathepsin S is a potent regulator of both cell and matrix turnover in advanced atherosclerosis', Arterioscler Thromb Vasc Biol, 29 (2), 188-94; Rodgers, K. J., et al. (2006), 'Destabilizing role of cathepsin S in murine atherosclerotic plaques', Arterioscler Thromb Vasc Biol, 26 (4), 851-6; Sukhova, G. K., et al. (2003), 'Deficiency of cathepsin S reduces atherosclerosis in LDL receptor-deficient mice', J Clin Invest, 111 (6), 897-906). This suggests a potential inhibitor of Cathepsin S would stabilise atherosclerotic plaque by reducing extracellular matrix breakdown, by reducing the proinflammatory state and by reducing accelerated calcification and subsequently its clinical manifestations.

These phenotypes described in atherosclerosis models are in agreement with known cellular functions of Cathepsin S. Firstly, Cathepsin S is involved in the degradation of extracellular matrix that stabilises the plaque. In particular, Cathepsin S has potent elastinolytic activity and can exert this at neutral pH, a feature that distinguishes Cathepsin S from all other Cathepsins. Secondly, Cathepsin S is the major protease involved in antigen processing, in particular cleavage of the invariant chain in antigen presenting cells (APCs), resulting in reduced contribution of T cells to the chronic inflammation of the atherosclerotic tissue. Elevated inflammation results in further oxidative and proteolytic tissue damage and subsequently plaque destabilisation (Cheng, X. W., et al. (2004), 'Increased expression of elastolytic cysteine proteases, cathepsins S and K, in the neointima of balloon-injured rat carotid arteries', Am J Pathol, 164 (1), 243-51; Driessen, C., et al. (1999), 'Cathepsin S controls the trafficking and maturation of MHC class II molecules in dendritic cells', J Cell Biol, 147 (4), 775-90; Rudensky, A. and Beers, C. (2006), 'Lysosomal cysteine proteases and antigen presentation', Ernst Schering Res Found Workshop, (56), 81-95).

The anti-inflammatory and anti-elastinolytic properties of a Cat S inhibitor make it also a prominent target for chronic obstructive pulmonary disease (Williams, A. S., et al. (2009), 'Role of cathepsin S in ozone-induced airway hyperresponsiveness and inflammation', Pulm Pharmacol Ther, 22 (1), 27-32). Furthermore due to its extracellular functions in matrix degradation, inhibition of cathepsin S will impact neointima formation and angiogenesis (Burns-Kurtis, C. L., et al. (2004), 'Cathepsin S expression is up-regulated following balloon angioplasty in the hypercholesterolemic rabbit', Cardiovasc Res, 62 (3), 610-20; Cheng, X. W., et al. (2004), 'Increased expression of elastolytic cysteine proteases, cathepsins S and K, in the neointima of balloon-injured rat carotid arteries', Am J Pathol, 164 (1), 243-51; Shi, G. P., et al. (2003), 'Deficiency of the cysteine protease cathepsin S impairs microvessel growth', Circ Res, 92 (5), 493-500; Wang, B., et al. (2006), 'Cathepsin S controls angiogenesis and tumor growth via matrix-derived angiogenic factors', J Biol Chem, 281 (9), 6020-9). An inhibitor of Cathepsin S might therefore be useful in several different disease settings.

Cathepsin S plays also a role in the reduction of tumor growth and tumor cell invasion as described by Roberta E. Burden in Clin Cancer Res 2009; 15(19). In addition, nephrectomized Cathepsin S knock out mice showed a significant reduction of arterial calcification when compared to nephrectomized wild type mice. This indicates that inhibition of Cathepsin S may have a beneficial effect on the reduction of cardiovascular events in chronic kidney disease patients (Elena Aikawa, Circulation, 2009, 1785-1794).

We have surprisingly found that inhibition of cathepsin S (CatS) with a CatS inhibitor reduced or prevented ADA formation to immunogenic compounds, in particular to immunomodulatory antibody drugs.

One of the early steps in the cycle of anti-tumor immunity is the capture and presentation of tumor-associated antigens by dendritic cells in the context of MHC-I or MHC-II molecules. Therefore, for cancer immunotherapy (CIT), it sounds counterintuitive to use a compound suppressing MHC-II maturation and antigen presentation. Nevertheless, recent studies have shown that the cathepsins upregulated in a wide range of cancers are associated with tumor growth, invasion and metastasis (Pogorzelska, Zolnowska et al., Biochimie, 2018, 85-106; Tan, Qian et al., Oncology Reports, 2018, 111-122). Taking this into account, inhibition of Cathepsin S with a CatS inhibitor can even play an additive effect, together with the immunomodulatory drug, in fighting cancer, by restoring the activity of the immunomodulatory anti-cancer drug and at the same time down-regulating cathepsin S.

BRIEF DESCRIPTION OF THE FIGURES

FIG. 1 represents the adalimumab-specific IgG response in hIgG1 Tg mice determined by ELISA before and after adalimumab immunization and administration of a cathepsin S inhibitor (dashed line) or vehicle (filled circles). The cathepsin S inhibitor reduces ADA to adalimumab in hIgG1 transgenic mice. Data shown represent mean±SEM of 10 mice/group. ***P<0.001.

FIGS. 2A-2B represent the CEA-specific IgG response in hIgG1 Tg mice (FIG. 2A) and wild-type mice (FIG. 2B) determined by ELISA before and after immunization with CEA-IL2v and administration of a cathepsin S inhibitor (dashed symbols) or vehicle (filled symbols). The cathepsin S inhibitor prevents ADA to CEA-IL2v in hIgG transgenic mice and reduces its levels in wild-type mice. Data shown represent mean±SEM of 10 mice/group. *P<0.01 and P<0.001, respectively.

FIG. 3 represents the high affinity NP-specific IgG response in wild-type mice determined by ELISA over time (x-axis). The high dose of cathepsin S inhibitor (40 mg/kg/day) significantly reduces NP-specific IgG levels compared to vehicle-treated animals. Data shown represent mean±SEM of 10 mice/group. ***P<0.001.

FIG. 4 represents the adalimumab-specific IgG response in hIgG1 Tg mice determined by ELISA over time (x-axis) before and after adalimumab immunization and administration of a cathepsin S inhibitor (dashed line) or vehicle (filled circles). The cathepsin S inhibitor reduces ADA to adalimumab in hIgG1 transgenic mice. Data shown represent mean±SEM of 10 mice/group. ***P<0.001.

FIGS. 5A-5B represent the CEA-specific IgG response in hIgG1 Tg mice (FIG. 2A) and wild-type mice (FIG. 2B) determined by ELISA over time (x-axis) before and after immunization with CEA-112v and administration of a cathepsin S inhibitor (dashed symbols) or vehicle (filled symbols). The cathepsin S inhibitor prevents ADA to CEA-IL2v in hIgG transgenic mice and reduces its levels in wild-type mice. Data shown represent mean±SEM of 10 mice/group. *P<0.001 and P<0.01, respectively.

FIGS. 6A-6B represent levels of CEA-IL2v in serum (y-axis) plotted over time (x-axis) in hIgG1 Tg mice (FIG. 6A) and wild-type mice (FIG. 6B). The CEA-IL2v exposure in cathepsin S inhibitor (dashed symbols) and vehicle (filled symbols) treated animals are shown. Data shown represent mean±SEM of 10 mice/group.

FIGS. 7A-7D represent the PD effect of CEA-IL2v in blood of hIgG1 Tg mice (FIGS. 7A and 7B) and. The percentages of TCRβ+CD8+CD8 T cells (FIGS. 7A and 7C) and NK1.1+ NKp46+ NK cells (FIGS. 7B and 7D) are depicted on the y-axis over time (x-axis). Data shown represent mean±SEM of 10 mice/group.

FIGS. 8A-8B represent the IgG response to murine surrogate FAP-OX40 in wild-type mice determined by ELISA. ADA specific to FAP (VHVL) is shown in FIG. 8A whereas OX40-specific ADA is shown in FIG. 8B. The cathepsin S inhibitor (dashed symbols) prevents ADA to FAP (FIG. 8A) as well as OX40 (FIG. 8B) domains in wild-type mice. Data shown represent mean±SEM of 10 mice/group. ***P<0.001.

FIG. 9 represents the IgG response to murine surrogate PD-L1 in wild-type mice determined by ELISA before and after PD-L1 immunization and administration of a cathepsin S inhibitor. The cathepsin S inhibitor significantly reduced ADA to mPD-L1 in wild-type mice. Data shown represent mean±SEM of 10 mice/group. ***P<0.001.

FIGS. 10A-10B represent the IgG response to murine hemi-surrogate CEA-TCB in hIgG1 Tg mice. CEA-specific ADA is shown in FIG. 10A whereas ADA specific to CD3 binder (2C11) is shown in FIG. 10B. Cathepsin S inhibitor (dashed symbols) and vehicle (filled symbols) treated animals are shown. The cathepsin S inhibitor significantly reduced ADA to CD3 binder (FIG. 10B), whereas the reduction of CEA-specific ADA was not significant compared to vehicle-treated animals (FIG. 10A). Data shown represent mean±SEM of 10 mice/group. **P<0.01.

The term "biologic", which can be changed with "biopharmaceutical", "biological medicinal product" or "biological", refers to any pharmaceutical drug product manufactured in, extracted from, or semisynthesized from biological sources. Different from totally synthesized pharmaceuticals, they include vaccines, blood, blood components, allergenics, somatic cells, gene therapies, tissues, recombinant therapeutic protein and living cells used in cell therapy. Biologics can be composed of sugars, proteins or nucleic acids or complex combinations of these substances, or may be living cells or tissues. They (or their precursors or components) are isolated from living sources—human, animal, plant, fungal or microbial.

The term "antibody" herein is used in the broadest sense and encompasses various antibody structures, including but not limited to monoclonal antibodies, polyclonal antibodies, multispecific antibodies (e.g. bispecific antibodies), and antibody fragments so long as they exhibit the desired antigen binding activity.

The terms "full length antibody," "intact antibody," and "whole antibody" are used herein interchangeably to refer to an antibody having a structure substantially similar to a native antibody structure.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2, diabodies, linear antibodies, single-chain antibody molecules (e.g. scFv), and single-domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific. See, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

A "Fab molecule" refers to a protein consisting of the VH and CH1 domain of the heavy chain (the "Fab heavy chain") and the VL and CL domain of the light chain (the "Fab light chain") of an immunoglobulin.

The term "bispecific" means that the antibody is able to specifically bind to at least two distinct antigenic determinants. Typically, a bispecific antibody comprises two antigen binding sites, each of which is specific for a different antigenic determinant. In certain embodiments the bispecific antibody is capable of simultaneously binding two antigenic determinants, particularly two antigenic determinants expressed on two distinct cells.

The term "T-cell bispecific antibody" refers to an antibody designed to simultaneously bind to a surface antigen on a target cell, e.g., a tumor cell, and to an activating, invariant component of the T cell receptor (TCR) complex, such as CD3, for retargeting of T cells to kill target cells. A T-cell bispecific antibody thus has an antigen binding moiety capable of forming an antigen binding moiety-antigen complex with an antigenic determinant found on the surface of T-cells.

A "BITE" (bispecific T cell engager) is a molecule wherein two scFv molecules are fused by a flexible linker (see, e.g., WO 2004/106381, WO 2005/061547, WO 2007/042261, and WO 2008/119567, Nagorsen and Bäuerle, Exp Cell Res 317, 1255-1260 (2011)).

The term "antibody-drug conjugate" (ADC) refers to an antibody which is conjugated to one or more therapeutic agents such as for example cytotoxic agents, chemotherapeutic agents, drugs, growth inhibitory agents, toxins (e.g., protein toxins, enzymatically active toxins of bacterial, fungal, plant, or animal origin, or fragments thereof) or radioactive isotopes. The antibody is typically connected to one or more of the therapeutic agents using linkers. An overview of ADC technology including examples of therapeutic agents and drugs and linkers is set forth in Pharmacol Review 68:3-19 (2016).

"Recombinant immunotoxins" are antibody-toxin chimeric molecules that kill cancer cells via binding to a surface antigen, internalization and delivery of the toxin moiety to the cell cytosol.

The term "immunogenicity", and hence "immunogenic", refers to the ability of a particular substance to provoke an immune response in the body of a human and other animal. In other words, immunogenicity is the ability to induce a humoral and/or cell-mediated immune responses. Distinction has to be made between wanted and unwanted immunogenicity. Wanted immunogenicity is typically related with vaccines, where the injection of an antigen (the vaccine) provokes an immune response against the pathogen (virus, bacteria . . . ) aiming at protecting the organism. Unwanted immunogenicity is an immune response by an organism against a therapeutic agent (ex. recombinant protein, or monoclonal antibody). This reaction leads to production of anti-drug-antibodies (ADA) inactivating the therapeutic effects of the treatment and, in somes cases, inducing adverse effects.

An "anti-drug antibody" or "ADA" refers to an antibody that binds to a therapeutic agent and may influence serum concentrations and function of the therapeutic agent in a subject. The presence of ADA may increase clearance of the therapeutic agent through formation of immune complexes between therapeutic agent and antibody (neutralizing, non-neutralizing or both), thus reducing the therapeutic agent's half-life. Furthermore, the activity and effectiveness of the therapeutic agent may be decreased through binding of antibody to the therapeutic agent (particularly in the case of neutralizing ADA). ADA can also be associated with allergic or hypersensitivity reactions and other adverse events as neutralization of host proteins.

The term "vector", as used herein, refers to an altered virus, including adeno-associated virus (AAV), where its viral genes are removed, not causing disease. Viral vectors such as rAAV are intended to transport missing or mutated genes to a cell in order to restore the function of the protein. As a consequence of its repetitive structure, viral vectors frequently induce humoral immunity characterized by generation of neutralizing antibodies, which represents the most effective barrier to successful gene transfer with AAV vectors.

The term "activity" refers to the beneficial pharmacological activity of a drug on living matter. Therefore, in the context of the present invention, the expression "increasing the activity of a therapeutic agent" refers in particular to the increase in beneficial pharmacological activity of said therapeutic agent. In the present invention, an increase in activity can be associated with or due to for example an increased exposure, increased half-life or increased bioavailability.

The term "bioavailability" refers to the fraction of an administered dose of unchanged drug that reaches the systemic circulation. In pharmacology, bioavailability is a measurement of the rate and extent to which a drug reaches at the site of action. Both definitions can be used in the context of the present invention.

The term "half-life" of a substance or therapeutic agent, in the present invention, is the time it takes for half of said substance or therapeutic agent to disappear from the target tissue or from the circulation.

The term "exposure" refers to the concentration of a drug in a body compartment (usually blood) as a function of time.

It is self-evident that the inhibitors are administered to the patient in a "therapeutically effective amount" (or simply "effective amount") which is the amount of the respective compound or combination that will elicit the biological or medical response of a tissue, system, animal or human that is being sought by the researcher, veterinarian, medical doctor or other clinician.

Examples of cathepsin S inhibitor useful in the present invention are described in They are described in WO 2010/121918 and WO2017/144483 which are herein incorporated by reference.

Advantageous cathepsin S inhibitor according to the invention are
(2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylicacid(1-cyano-cyclopropyl)-amide; or
(2S,4R)-4-[4-(5-methyl-tetrazol-2-yl)-2-trifluoromethyl-benzenesulfonyl]-1-(1-trifluoromethyl-cyclopropanecarbonyl)-pyrrolidine-2-carboxylicacid(1-cyano-cyclopropyl)-amide;
or a pharmaceutically acceptable salt thereof;
They are described in WO 2010/121918 and WO2017/144483. They are represented below.

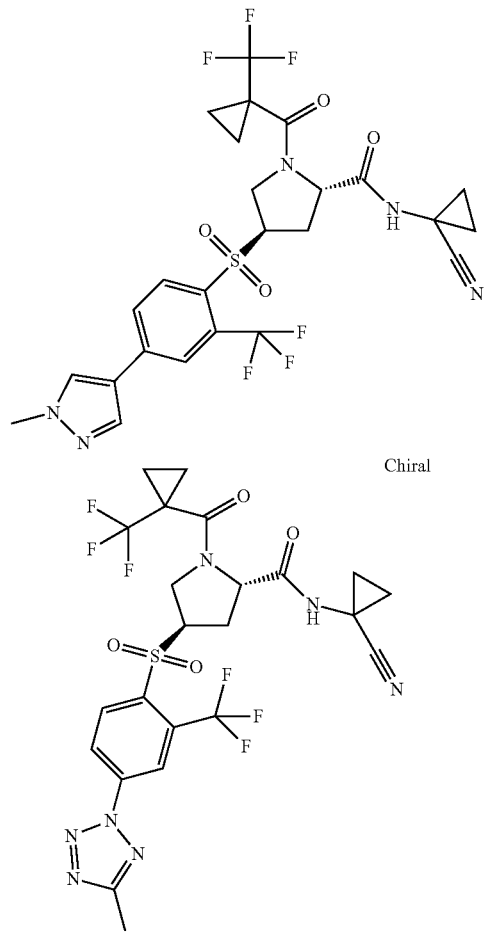

Chiral (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide is a particular advantageous cathepsin S inhibitor according to the invention.

Among the therapeutic agents that benefit most of the invention are antibodies, in particular antibodies used in oncology, more particularly immune activating compounds, e.g. cancer immunotherapy agents, including check point inhibitory antibodies like for example anti-PD-L1 or anti-PD-1 antibodies, for example atezolizumab, durvalumab, avelumab, pembrolizumab or nivolumab.

T-cell bispecific antibodies, BiTEs, cytokines, immunocytokines and immunomodulatory antibodies are particular examples of such therapeutic agents. Antibodies used in ophtlamology (e.g. Lucentis®), diabetes (Lantus®) or inflammatory and autoimmune diseases also benefit from the invention.

Examples of therapeutic agents according to the invention are alemtuzumab (LEMTRADA®), atezolizumab (TECENTRIQ®), bevacizumab (AVASTIN®), cetuximab (ERBITUX®), panitumumab (VECTIBIX®), pertuzumab (OMNITARG®, 2C4), trastuzumab (EIERCEPTIN®), tositumomab (Bexxar®), abciximab (REOPRO®), adalimumab (HUMIRA®), apolizumab, aselizumab, atlizumab, bapineuzumab, basiliximab (SIMULECT®), bavituximab, belimumab (BENLYSTA®) briankinumab, canakinumab (ILARIS®), cedelizumab, certolizumab pegol (CIMZIA®), cidfusituzumab, cidtuzumab, cixutumumab, clazakizumab, crenezumab, daclizumab (ZENAPAX®), dalotuzumab, denosumab (PROLIA®, XGEVA®), eculizumab (SOLIRIS®), efalizumab, emicizumab (HEMLIBRA®), epratuzumab, erlizumab, felvizumab, fontolizumab, golimumab (SIMPONI®), ipilimumab, imgatuzumab, infliximab (REMICADE®), labetuzumab, lebrikizumab, lexatumumab, lintuzumab, lucatumumab, lulizumab pegol, lumretuzumab, mapatumumab, matuzumab, mepolizumab, mogamulizumab, motavizumab, motovizumab, muronomab, natalizumab (TYSABRI®), necitumumab (PORTRAZZA®), nimotuzumab (THERACIM®), nolovizumab, numavizumab, obinutuzumab (GAZYVA®/GAZYVARO®), ocrelizumab (OCREVUS®), olokizumab, omalizumab (XOLAIR®), onartuzumab (also known as MetMAb), palivizumab (SYNAGIS®), pascolizumab, pecfusituzumab, pectuzumab, pegylated interferon (PEGAZYS®), pembrolizumab (KEYTRUDA®), pexelizumab, priliximab, ralivizumab, ranibizumab (LUCENTIS®), reslivizumab, reslizumab, resyvizumab, rituximab (MABTHERA®), robatumumab, rontalizumab, rovelizumab, ruplizumab, sarilumab, secukinumab, seribantumab, sifalimumab, sibrotuzumab, siltuximab (SYLVANT®) siplizumab, sontuzumab, tadocizumab, talizumab, tefibazumab, tocilizumab (ACTEMRA®), toralizumab, trastuzumab emtansine (KADCYLA®), tucusituzumab, umavizumab, urtoxazumab, ustekinumab (STELARA®), vedolizumab (ENTYVIO®), visilizumab, zanolimumab and zalutumumab.

In the above list and in the rest of the application, tradenames are indicated in brackets for illustrative purposes. It is understood that the INN defines the therapeutic agents according to the invention, therefore covering also the biosimilars of the originator products.

Particular therapeutic agents according to the invention are IgG antibodies, in particular human IgG antibodies, IgG1 antibodies, in particular human, humanized or chimeric IgG1 antibodies, IgG1 antibody-drug conjugates, in particular chimeric IgG1 antibody-drug conjugates, IgG2 antibodies, in particular human or humanized IgG2 antibodies, IgG4 antibodies, in particular human or humanized IgG4 antibodies, IgG2/4 antibodies, in particular human or humanized IgG2/4 antibodies, Fab fragments, in particular IgG Fab fragments or IgG1 Fab fragments, in particular humanized IgG Fab fragments or humanized or chimeric IgG1 Fab fragments, humanized IgG4-toxin conjugate, human monoclonal antitoxin antibodies, humanized IgG4-toxin conjugates or recombinant immunotoxins.

Antibody-drug conjugates are a particular type of therapeutic agent according to the invention.

Particular therapeutic agents according to the invention are antibodies against GPIIb/IIIa, TNF-alpha, CD-52, PCSK-9, PD-L1, CD-25, BLyS, CD-125, VEGF, *C. difficile* Toxin B, CD-30, IL-17RA, IL-1β, PD-1, EGFR, CD-38, RANKL, IL-4Ralpha, Complement C5, SLAMF7, Factor VIII, CGRPR, CGRP, CD-33, CD-4, CTLA-4, IL-5, CCR4, CD-22, VLA-4, CD-20, PDGFR-alpha, IgE, F-protein of RS virus, HER-2, VEGF-A, IL-17a, cCLB8, IL-23, IL-6 receptor, IL-12, IL-23, Integrin-alpha4b7, CEA or CD3.

Particular therapeutic agents according to the invention are the following antibodies: abciximab, adalimumab, alemtuzumab, alirocumab, atezolizumab, avelumab, basiliximab, belimumab, benralizumab, bevacizumab, bezlotoxumab, brentuximab, brodalumab, canakinumab, catumaxomab, cemiplimab, certolizumab pegol, cetuximab, daratumumab, denosumab, dupilumab, durvalumab, eculizumab, elotuzumab, emicizumab, erenumab, etanercept, evolocumab, fremanezumab, galcanezumab, gemtuzumab ozogamicin, golimumab, ibalizumab, infliximab, ipilimumab, mepolizumab, mogamulizumab, moxetumomab, natalizumab, necitumumab, nivolumab, obinutuzumab, ocrelizumab, ofatumumab, olaratumab, omalizumab, palivizumab, panitumumab, pembrolizumab, pertuzumab, ramucirumab, ranibizumab, reslizumab, rituximab, secukinumab, siltuximab, tildrakizumab, tocilizumab, trastuzumab, ustekinumab and vedolizumab.

Other particular therapeutic agents according to the invention are protein products, like for example interferon-gamma, interferon-beta, erythropoietin, antihemophilic factor VIII, CD-2 inhibitor, coagulation factor Xa, Interferon-beta mimetic, follicle-stimulating hormone, GLP-1 agonist, b-glucocerebrosidase mimetic, erythropoietin mimetic, KGF mmetic, insulin mimetic, acid alpha-glucosidase mimetic, G-CSF mimetic, IL-11 mimetic, CD-80/86 blocker, metabolizing enzyme, IL-2 mimetic, rhDNAse, fibrin sealant of wounds or direct thrombin inhibitor.

Particular therapeutic agents according to the invention are the following proteins: Alteplase, Octocog alfa, Alefacept, Andexxa, Interferon Beta-1a, Interferon beta-1b, Urofollitropin, Exenatide, Alglucerase, Idursulfase, Eloctate, Epoetin alfa, Palifermin, Insulin detemir, Alglucosidase alfa, Pegfilgrastim, Neumega, Belatacept, Pegvaliase, Aldesleukin, Dornase alfa, Raplixa, ReFacto, Lepirudin or Albiglutide.

Further particular therapeutic agents according to the invention are protein replacement therapies, like for example recombinant human acid aslpha-glucosidase (rhGAA), factor VIII or interferon beta.

Adalimumab (HUMIRA®) is a particular therapeutic agent for use in the invention. It is used to treat rheumatoid arthritis, psoriatic arthritis, ankylosing spondylitis, Crohn's disease, ulcerative colitis, chronic psoriasis, hidradenitis suppurativa and juvenile idiopathic arthritis. Adalimumab is a TNF-inhibiting, anti-inflammatory, biologic medication. It binds to tumor necrosis factor-alpha (TNFα), which normally binds to TNFα receptors, leading to the inflammatory response of autoimmune diseases. By binding to TNFα, adalimumab reduces this inflammatory response. Because TNFα is also part of the immune system, which protects the body from infection, treatment with adalimumab may increase the risk of infections. Like other TNF inhibitors, it is an immunomodulatory medication, used to treat autoimmune diseases such as rheumatoid arthritis. It is associated with high incidence of immunogenicity in clinical trials (Bartelds G M et al, Ann Rheum Dis, 2007, 921-926; Bartelds G M et at, JAMA, 2011, 146-1468). It cross-reacts with mouse TNF leading to high ADA responses (Bitoun S et al, Ann Rheum Dis, 2018, 1463-1470), thus Adalimumab is a suitable model compound to demonstrate the efficacy of the present invention in pre-clinical mouse models.

Cergutuzumab amunaleukin (CEA-IL2v, RG7813) is a particular therapeutic agent for use in the invention. It is a monomeric CEA-targeted immunocytokine that comprises a single IL-2 variant (IL2v) moiety with abolished CD25 binding, fused to the C-terminus of a high affinity, bivalent carcinoembryonic antigen (CEA)-specific antibody devoid of Fc-mediated effector functions. It is described in WO 2012/107417 and WO 2012/146628.

T cell activating bispecific antibodies are a novel class of cancer therapeutics, designed to engage cytotoxic T cells against tumor cells. The simultaneous binding of such an antibody to CD3 on T cells and to an antigen expressed on the tumor cells will force a temporary interaction between tumor cell and T cell, causing activation of the T cell and subsequent lysis of the tumor cell. They are particular therapeutic agents according to the invention.

CEA TCB (RG7802, R06958688, cibisatamab) is a novel T cell activating bispecific antibody targeting CEA on tumor cells and CD3E on T cells. In mouse models, CEA TCB displays potent anti-tumor activity, leads to increased intra-tumoral T cell infiltration, increased release of pro-inflammatory cytokines such as IFNγ, TNF and Granzyme B, and up-regulates the PD-L1/PD-1 pathway and its activation. The increase in PD-L1/PD-1 pathway is a sign of fully activated T cells as it is one of the suppressive pathways that is turned on during T cell activation. It is a particular therapeutic agent according to the invention.

FAP-OX40 (R07194691) is a bispecific antibody construct in development. It simultaneously binds to Fibroblast activation protein (FAP) highly expressed on stroma cells in various solid tumors and the activation induced T-cell specific surface molecule OX40. The mode of action relies on FAP binding (tumor specific targeting) and stimulation of OX40 expressing tumor infiltrating T-cells; thus enhancing the T-cell mediated immune response (cytokine secretion, expansion) against tumor cells in patients. It is in particular described in WO 2017/060144 and WO 2019/086497. It comprises a first heavy chain comprising an amino acid sequence of SEQ ID NO:1, a second heavy chain comprising an amino acid sequence of SEQ ID NO:2, and four light chains comprising an amino acid sequence of SEQ ID NO:3. It is a particular therapeutic agent according to the invention. The murine antibody used in the examples has a first heavy chain comprising an amino acid sequence of SEQ ID NO:4, a second heavy chain comprising an amino acid sequence of SEQ ID NO:5, and four light chains comprising an amino acid sequence of SEQ ID NO:6.

TABLE 1

Sequences

| SEQ ID NO: | Name | Sequence |
|---|---|---|
| 1 | HC 1 (49B4) VHCH1_VHCH1 Fc knob VH (4B9) | QVQLVQSGAEVKKPGSSVKVSCKASGGTFS SYAISWVRQAPGQGLEWMGGIIPIFGTANYA QKFQGRVTITADKSTSTAYMELSSLRSEDTA VYYCAREYYRGPYDYWGQGTTVTVSSAST KGPSVFPLAPSSKSTSGGTAALGCLVKDYFP EPVTVSWNSGALTSGVHTFPAVLQSSGLYSL SSVVTVPSSSLGTQTYICNVNEIKPSNTKVDK KVEPKSCDGGGSGGGGSQVQLVQSGAEV KKPGSSVKVSCKASGGTFSSYAISWVRQAPG QGLEWMGGIIPIFGTANYAQKFQGRVTITAD KSTSTAYMELSSLRSEDTAVYYCAREYYRG PYDYWGQGTTVTVSSASTKGPSVFPLAPSSK STSGGTAALGCLVKDYFPEPVTVSWNSGAL TSGVHTFPAVLQSSGLYSLSSVVTVPSSSLGT QTYICNVNEIKPSNTKVDKKVEPKSCDKTHT CPPCPAPEAAGGPSVFLFPPKPKDTLMISRTP EVTCVVVDVSEEEDPEVKFNWYVDGVEVHN AKTKPREEQYNSTYRVVSVLTVLHQDWLN GKEYKCKVSNKALGAPIEKTISKAKGQPREP QVYTLPPCRDELTKNQVSLWCLVKGFYPSDI AVEWESNGQPENNYKTTPPVLDSDGSFFLYS KLTVDKSRWQQGNVFSCSVMHEALHNHYT QKSLSLSPGGGGSGGGGSGGGGSGGGSE VQLLESGGGLVQPGGSLRLSCAASGFTFSSY AMSWVRQAPGKGLEWVSAIIGSGASTYYAD SVKGRFTISRDNSKNTLYLQMNSLRAEDTA VYYCAKGWFGGFNYWGQGTLVTVSS |
| 2 | HC 2 (49B4) VHCH1_VHCH1 Fc hole VL (4B9) | QVQLVQSGAEVKKPGSSVKVSCKASGGTFS SYAISWVRQAPGQGLEWMGGIIPIFGTANYA QKFQGRVTITADKSTSTAYMELSSLRSEDTA VYYCAREYYRGPYDYWGQGTTVTVSSAST KGPSVFPLAPSSKSTSGGTAALGCLVKDYFP EPVTVSWNSGALTSGVHTFPAVLQSSGLYSL SSVVTVPSSSLGTQTYICNVNEIKPSNTKVDK KVEPKSCDGGGGSGGGGSQVQLVQSGAEV KKPGSSVKVSCKASGGTFSSYAISWVRQAPG QGLEWMGGIIPIFGTANYAQKFQGRVTITAD KSTSTAYMELSSLRSEDTAVYYCAREYYRG PYDYWGQGTTVTVSSASTKGPSVFPLAPSSK STSGGTAALGCLVKDYFPEPVTVSWNSGAL TSGVHTFPAVLQSSGLYSLSSVVTVPSSSLGT QTYICNVNEIKPSNTKVDKKVEPKSCDKTHT CPPCPAPEAAGGPSVFLFPPKPKDTLMISRTP EVTCVVVDVSEEDPEVKFNWYVDGVEVHN AKTKPREEQYNSTYRVVSVLTVLHQDWLN GKEYKCKVSNKALGAPIEKTISKAKGQPREP QVCTLPPSRDELTKNQVSLSCAVKGFYPSDI AVEWESNGQPENNYKTTPPVLDSDGSFFLVS KLTVDKSRWQQGNVFSCSVMHEALHNHYT QKSLSLSPGGGGSGGGGSGGGGSGGGSEI VLTQSPGTLSLSPGERATLSCRASQSVTSSYL |

TABLE 1-continued

Sequences

| SEQ ID NO: | Name | Sequence |
|---|---|---|
| | | AWYQQKPGQAPRLLINVGSRRATGIPDRFSG SGSGTDFTLTISRLEPEDFAVYYCQQGIMLPP TFGQGTKVEIK |
| 3 | LC (49B4) | DIQMTQSPSTLSASVGDRVTITCRASQSISSW LAWYQQKPGKAPKLLIYDASSLESGVPSRFS GSGSGTEFTLTISSLQPDDFATYYCQQYSSQP YTFGQGTKVEIKRTVAAPSVFIFPPSDEQLKS GTASVVCLLNNFYPREAKVQWKVDNALQS GNSQESVTEQDSKDSTYSLSSTLTLSKADYE KHKVYACEVTHQGLSSPVTKSFNRGEC |
| 4 | HC 1 (P1AD4396) | QVQLKESGPGLVQPSQTLSLTCTVSGFSLTG YNLHWVRQPPGKGLEWMGRMRYDGDTYY NSVLKSRLSISRDTSKNQVFLKMNSLQTDDT AIYYCTRDGRGDSFDYWGQGVMVTVSSAK TTPPSVYPLAPGSAAQTNSMVTLGCLVKGY FPEPVTVTWNSGSLSSGVHTFPAVLQSDLYT LSSSVTVPSSTWPSQTVTCNVARPASSTKVD KKIVPRDCGGGSGGGGSQVQLKESGPGLV QPSQTLSLTCTVSGFSLTGYNLHWVRQPPGK GLEWMGRMRYDGDTYYNSVLKSRLSISRDT SKNQVFLKMNSLQTDDTAIYYCTRDGRGDS FDYWGQGVMVTVSSAKTTPPSVYPLAPGSA AQTNSMVTLGCLVKGYFPEPVTVTWNSGSL SSGVHTFPAVLQSDLYTLSSSVTVPSSTWPS QTVTCNVAIIPASSTKVDKKIVPRDCGCKPCI CTVPEVSSVFIFPPKPKDVLTITLTPKVTCVV VAISKDDPEVQFSWFVDDVEVHTAQTKPRE EQINSTFRSVSELPIMHQDWLNGKEFKCRVN SAAFGAPIEKTISKTKGRPKAPQVYTIPPPKK QMAKDKVSLTCMITNFFPEDITVEWQWNGQ PAENYKNTQPMKTDGSYFVYSKLNVQKSN WEAGNTFTCSVLIIEGLHNIITITEKSLSHSPG GGGGSGGGGSGGGGSGGGGSEVQLLESGG GLVQPGGSLRLSCAASGFTFSSHAMSWVRQ APGKGLEWVSAIWASGEQYYADSVKGRFTI SRDNSKNTLYLQMNSLRAEDTAVYYCAKG WLGNFDYWGQGTLVTVSS |
| 5 | HC2 (P1AD4396) | QVQLKESGPGLVQPSQTLSLTCTVSGFSLTG YNLHWVRQPPGKGLEWMGRMRYDGDTYY NSVLKSRLSISRDTSKNQVFLKMNSLQTDDT AIYYCTRDGRGDSFDYWGQGVMVTVSSAK TTPPSVYPLAPGSAAQTNSMVTLGCLVKGY FPEPVTVTWNSGSLSSGVHTFPAVLQSDLYT LSSSVTVPSSTWPSQTVTCNVARPASSTKVD KKIVPRDCGGGGSGGGGSQVQLKESGPGLV QPSQTLSLTCTVSGFSLTGYNLHWVRQPPGK GLEWMGRMRYDGDTYYNSVLKSRLSISRDT SKNQVFLKMNSLQTDDTAIYYCTRDGRGDS FDYWGQGVMVTVSSAKTTPPSVYPLAPGSA AQTNSMVTLGCLVKGYFPEPVTVTWNSGSL SSGVHTFPAVLQSDLYTLSSSVTVPSSTWPS QTVTCNVARPASSTKVDKKIVPRDCGCKPCI CTVPEVSSVFIFPPKPKDVLTITLTPKVTCVV VAISKDDPEVQFSWFVDDVEVHTAQTKPRE EQINSTFRSVSELPIMHQDWLNGKEFKCRVN SAAFGAPIEKTISKTKGRPKAPQVYTIPPPKE QMAKDKVSLTCMITNFFPEDITVEWQWNGQ PAENYDNTQPWEDTDGSYFVYSDLNVQKSN WEAGNTFTCSVLREGLHNEEHTEKSLSHSPG GGGGSGGGGSGGGGSGGGGSEIVLTQSPGT LSLSPGERATLSCRASQSVSRSYLAWYQQKP GQAPRLLIIGASTRATGIPDRFSGSGSGTDFT LTISRLEPEDFAVYYCQQGQVIPPTFGQGTK VEIK |
| 6 | LC (P1AD4396) | DIVMTQGALPNPVPSGESASITCRSSQSLVYK DGQTYLNWFLQRPGQSPQLLTYWMSTRAS GVSDRFSGSGSGTYFTLKISRVRAEDAGVYY CQQVREYPFTFGSGTKLEIKRADAAPTVSIFP PSSEQLTSGGASVVCFLNNFYPKDINVKWKI DGSERQNGVLNSWTDQDSKDSTYSMSSTLT |

TABLE 1-continued

Sequences

| SEQ ID NO: | Name | Sequence |
|---|---|---|
| | | LTKDEYERHNSYTCEATHKTSTSPIVKSFNRNEC |

Atezolizumab (MPDL3280A, trade name Tecentriq®) is a fully humanized, engineered monoclonal antibody of IgG1 isotype against the protein programmed cell death-ligand 1 (PD-L1) and is a particular therapeutic agent according to the invention.

Infliximab (REMICADE®) and adalimuab (HUMIRA®) are particular therapeutic agents according to the invention since they are both known to be highly immunogenic. They are anti-TNFalpha antibodies indicated in particular for the treatment of Crohn's disease, ulcerative colitis, psoriasis, psoriatic arthritis, ankylosing spondylitis and rheumatoid arthritis (infliximab) and rheumatoid arthritis, psoriatic arthritis, ankylosing spondylitis, Crohn's disease, ulcerative colitis, psoriasis, hidradenitis suppurativa, uveitis and juvenile idiopathic arthritis (adalimumab).

Crohn's disease and ulcerative colitis are the principal forms of inflammatory bowel disease (IBD). IBD is a severely debilitating disease that impacts in particular young patients. It can cause bloody diarrhea with urgency, repeated flares, abdominal pain and can necessitate frequent surgical interventions and hospitalizations. The disease burden comprises bowel perforation, toxic megacolon, fistulae, strictures, infertility, abscesses and ileostomy. Patients with IBD have an increased risk of colon cancer, high rates of depression, anxiety, increased suicide, high rates of severe fatigue (47%), disability (34%), and chronic pain (38%).

The currently available treatments of IBD comprise anti-TNFalpha antibodies like infliximab and adalimumab, anti-α4β7 integrin antibodies like vedolizumab, anti-p40 antibodies like ustekinumab, JAK1 or JAK3i inhibitors like tofacitinib and anti-IL23 antibodies like risankizumab as therapeutic agents.

However, no broad sustained remission is observed with only 10-20% of patients remaining in remission at 1 year of treatment. The onset of some of the above therapeutic agents is slow, taking up to 12 weeks. Low rates of endoscopic and histologic healing are observed, together with increased risk of serious infection and malignancy. And furthermore, the current standard of care, infliximab and adalimumab, generate a high immunogenicity, with reported immunogenicity rates of up to 51% and 26%, respectively.

Efficiently treating IBD remains in consequence a high unmet medical.

Since administering a cathepsin S according to the invention reduces or prevents the formation of anti-drug antibodies (ADA) against a therapeutic agent in a subject who is receiving a treatment with said therapeutic agent, the cathepsin S inhibitor is particularly useful in the treatment of IBD.

The cathepsin S inhibitor according to the invention, in particular the two specific cathepsin S inhibitors described above, can be administered at a dose of between 50 mg/kg/day and 400 mg/kg/day, in particular between 75 mg/kg/day and 250 mg/kg/day, more particularly at 100 mg/kg/day or 200 mg/kg/day.

The cathepsin S inhibitor according to the invention, in particular the two specific cathepsin S inhibitors described above, are particularly advantageously administered at dose of 200 mg/kg/day, in particular 100 mg/kg b.i.d.

100 mg/kg b.i.d has been established as the safest and most efficacious dose of the cathepsin S inhibitor in human according to the invention, in particular for the two specific cathepsin S inhibitors described above. The doses employed in the examples have been adapted to the murine species.

The first dose of the cathepsin S inhibitor is advantageously administered to the subject prior to the first dose of the therapeutic agent, in particular between at least 1 day and 2 weeks before the first dose of the therapeutic agent, in particular between at least 1 day and 1 week before the first dose of the therapeutic agent, more particularly 1 week before the first dose of the therapeutic agent.

It is therefore understood that the expression "a patient who is receiving a treatment with a therapeutic agent" encompasses patient who are about to start a treatment with said therapeutic agent and which will be dosed with the cathepsin S inhibitor prior to the first dose of the therapeutic agent.

The invention thus relates in particular to:

A cathepsin S inhibitor for use in a method for reducing or preventing the formation of anti-drug antibodies (ADA) against a therapeutic agent in a subject who is receiving a treatment with said therapeutic agent;

A method for reducing or preventing the formation of anti-drug antibodies (ADA) against a therapeutic agent in a patient in need thereof who is receiving a treatment with said therapeutic agent, comprising administering an effective amount of a cathepsin S inhibitor to said patient;

A cathepsin S inhibitor for use in a method for increasing the activity of a therapeutic agent in a patient who is receiving a treatment with said therapeutic agent, wherein the activity of said therapeutic agent has been reduced by the subject's immune system;

A method for increasing the activity of a therapeutic agent in a subject who is receiving a treatment with said therapeutic agent, wherein the activity of said therapeutic agent has been reduced by the subject's immune system, comprising the administration of an effective amount of a cathepsin S inhibitor to said patient;

A cathepsin S inhibitor for use in a method for increasing the activity of a therapeutic agent in a patient who is receiving a treatment with said therapeutic agent, wherein the therapeutic agent has a lower activity in the absence of said cathepsin S inhibitor;

A method for increasing the activity of a therapeutic agent in a subject who is receiving a treatment with said therapeutic agent, comprising the administration of an effective amount of a cathepsin S inhibitor to said patient, wherein the therapeutic agent has a lower activity in the absence of said cathepsin S inhibitor;

A cathepsin S inhibitor for use in a method for increasing the bioavailability of a therapeutic agent in a patient who is receiving a treatment with said therapeutic agent;

A method for increasing the bioavailability of a therapeutic agent in a patient in need thereof who is receiving a treatment with said therapeutic agent, comprising the administration of an effective amount of a cathepsin S inhibitor to said patient;

A method for treating or preventing a disease comprising administering an effective amount of a therapeutic agent against said disease to a patient in need thereof and of a cathepsin S inhibitor, wherein the cathepsin S inhibitor is administered in an amount that is sufficient to reduce or prevent the formation of ADA against said therapeutic agent;

The use of a cathepsin S inhibitor in the manufacture of a medicament for reducing or preventing the formation of anti-drug antibodies (ADA) against a therapeutic agent in a subject who is receiving a treatment with said therapeutic agent;

A method for reducing or preventing the formation of anti-drug antibodies (ADA) against a therapeutic agent in a patient in need thereof who is receiving a treatment with said therapeutic agent comprising administering an effective amount of a cathepsin S inhibitor to said patient;

The use of a cathepsin S inhibitor in the manufacture of a medicament for increasing the activity of a therapeutic agent in a subject who is receiving a treatment with said therapeutic agent, wherein the activity of said therapeutic agent has been reduced by the subject's immune system;

The use of a cathepsin S inhibitor in the manufacture of a medicament for increasing the activity of a therapeutic agent in a subject who is receiving a treatment with said therapeutic agent, wherein the therapeutic agent has a lower activity in the absence of said cathepsin S inhibitor;

The use of a cathepsin S inhibitor in the manufacture of a medicament for increasing the bioavailability of a therapeutic agent in a subject who is receiving a treatment with said therapeutic agent;

A kit for the prevention or reduction of the formation of ADA against a therapeutic agent in a subject, wherein the kit comprises a cathepsin S inhibitor and instructions for using the cathepsin S inhibitor in a method of treatment comprising the administration of the cathepsin S inhibitor and the therapeutic agent to said subject;

A kit for the prevention or treatment of a disease in a subject, wherein the kit comprises a therapeutic agent and instructions for using the therapeutic agent in a method of treatment comprising the administration of a cathepsin S inhibitor and the therapeutic agent to said subject;

A kit according to the invention comprising:
(a) a therapeutic agent;
(b) a cathepsin S inhibitor; and
(c) instructions for using the therapeutic agent and the cathepsin S inhibitor in a method of treatment comprising the administration of effective amounts of said therapeutic agent and said cathepsin S inhibitor to a patient in need thereof;

A kit according to the invention wherein the cathepsin S inhibitor is administered in an amount that is sufficient to reduce or prevent the formation of ADA against the therapeutic agent;

A cathepsin S inhibitor for use in the treatment of IBD;

A method of treatment of IBD, comprising administering an effective amount of a cathepsin S inhibitor to a patient in need thereof;

A cathepsin S inhibitor for use in the treatment of IBD in a patient who is receiving a treatment with a therapeutic agent;

A method of treatment of IBD, comprising administering an effective amount of a cathepsin S inhibitor to a patient in need thereof, wherein the patient is receiving a treatment with a therapeutic agent;

A cathepsin S inhibitor for use, a method, a use or a kit according to the invention, wherein the first dose of the cathepsin S inhibitor is administered to the subject before the first dose of the therapeutic agent;

A cathepsin S inhibitor for use, a method, a use or a kit according to the invention, wherein the method or the instructions comprise the following consecutive steps:
(a) administering a first effective dose of the cathepsin S inhibitor to the subject;
(b) optionally continuing the administration of the cathepsin S inhibitor before the therapeutic agent is administered to the subject;
(c) administering a first effective dose of the therapeutic agent to the subject; and
(d) continuing the administration of the cathepsin S inhibitor and/or the therapeutic agent to the subject;

A cathepsin S inhibitor for use, a method, a use or a kit according to the invention, wherein the first dose of the cathepsin S inhibitor is administered to the subject prior to the first dose of the therapeutic agent, in particular between at least 1 day and 2 weeks before the first dose of the therapeutic agent, in particular between at least 1 day and 1 week before the first dose of the therapeutic agent, more particularly 1 week before the first dose of the therapeutic agent;

A cathepsin S inhibitor for use, a method, a use or a kit according to the invention, wherein the first dose of the cathepsin S inhibitor is administered to the subject on the same day as the first dose of the therapeutic agent;

A cathepsin S inhibitor for use, a method, a use or a kit according to the invention, wherein the therapeutic agent does not interfere with the MHC-II antigen presentation;

A cathepsin S inhibitor for use, a method, a use or a kit according to the invention, wherein the therapeutic agent does not rely on MHC-II antigen presentation;

A cathepsin S inhibitor for use, a method, a use or a kit according to the invention, wherein the ADA are produced through a T-cell dependent immune response;

A cathepsin S inhibitor for use, a method, a use or a kit according to the invention, wherein the ADA are produced through a T-helper cell dependent immune response;

A cathepsin S inhibitor for use, a method, a use or a kit according to the invention, wherein the ADA are produced by a MHC-II dependent immune response;

A cathepsin S inhibitor for use, a method, a use or a kit according to the invention, wherein the ADA are produced from a cognate interaction between an WW-II/peptide complex and a T-cell receptor;

A cathepsin S inhibitor for use, a method, a use or a kit according to the invention, wherein the therapeutic agent is a biologic, in particular a protein, more particularly a polypeptide, an antibody, more particularly a bispecific antibody, in particular a T-cell bispecific antibody, an antibody fragment, an antibody-drug conjugate, a BiTE, a cytokine or a gene therapy vectors like for example AAV vector;

A cathepsin S inhibitor for use, a method, a use or a kit according to the invention, wherein the therapeutic agent is an immune activating compound, in particular a cancer immunotherapy agent, including check point inhibitory antibodies.

A cathepsin S inhibitor for use, a method, a use or a kit according to the invention, wherein the therapeutic agent is an anti-PD-L1 antibody, like for example, atezolizumab, durvalumab oravelumab, in particular atezolizumab;

A cathepsin S inhibitor for use, a method, a use or a kit according to the invention, wherein the therapeutic agent is an anti-PD-1 antibody, like for example, nivolumab or pembrolizumab;

A cathepsin S inhibitor for use, a method, a use or a kit according to the invention, wherein the therapeutic agent is a biologic which induces, enhances or suppresses an immune response;

A cathepsin S inhibitor for use, a method, a use or a kit according to the invention, wherein the therapeutic agent is immunogenic;

A cathepsin S inhibitor for use, a method, a use or a kit according to the invention, wherein the therapeutic agent is indicated for the treatment of cancer, a metabolic disease like e.g. diabetes, an eye disease, an autoimmune or inflammatory disease;

A cathepsin S inhibitor for use, a method, a use or a kit according to the invention, wherein the therapeutic agent is indicated for the treatment of inflammatory bowel disease;

A cathepsin S inhibitor for use, a method, a use or a kit according to the invention, wherein the therapeutic agent is a monoclonal antibody, in particular a monoclonal antibody selected from alemtuzumab (LEMTRADA®), atezolizumab (TECENTRIQ®), bevacizumab (AVASTIN®), cetuximab (ERBITUX®), panitumumab (VECTIBIX®), pertuzumab (OMNITARG®, 2C4), trastuzumab (HERCEPTIN®), tositumomab (Bexxar®), abciximab (REOPRO®), adalimumab (HUMIRA®), apolizumab, aselizumab, atlizumab, bapineuzumab, basiliximab (SIMULECT®), bavituximab, belimumab (BENLYSTA®) briankinumab, canakinumab (ILARIS®), cedelizumab, certolizumab pegol (CIMZIA®), cidfusituzumab, cidtuzumab, cixutumumab, clazakizumab, crenezumab, daclizumab (ZENAPAX®), dalotuzumab, denosumab (PROLIA®, XGEVA®), eculizumab (SOLIRIS®), efalizumab, emicizumab (HEMLIBRA®), epratuzumab, erlizumab, felvizumab, fontolizumab, golimumab (SIMPONI®), ipilimumab, imgatuzumab, infliximab (REMICADE®), labetuzumab, lebrikizumab, lexatumumab, lintuzumab, lucatumumab, lulizumab pegol, lumretuzumab, mapatumumab, matuzumab, mepolizumab, mogamulizumab, motavizumab, motovizumab, muronomab, natalizumab (TYSABRI®), necitumumab (PORTRAZZA®), nimotuzumab (THERACIM®), nolovizumab, numavizumab, obinutuzumab (GAZYVA®/GAZYVARO®), ocrelizumab (OCREVUS®), olokizumab, omalizumab (XOLAIR®), onartuzumab (also known as MetMAb), palivizumab (SYNAGIS®), pascolizumab, pecfusituzumab, pectuzumab, pegylated interferon (PEGAZYS®), pembrolizumab (KEYTRUDA®), pexelizumab, priliximab, ralivizumab, ranibizumab (LUCENTIS®), reslivizumab, reslizumab, resyvizumab, rituximab (MABTHERA®), robatumumab, rontalizumab, rovelizumab, ruplizumab, sarilumab, secukinumab, seribantumab, sifalimumab, sibrotuzumab, siltuximab (SYLVANT®) siplizumab, sontuzumab, tadocizumab, talizumab, tefibazumab, tocilizumab (ACTEMRA®), toralizumab, trastuzumab emtansine (KADCYLA®), tucusituzumab, umavizumab, urtoxazumab, ustekinumab (STELARA®), vedolizumab (ENTYVIO®), visilizumab, zanolimumab and zalutumumab;

A cathepsin S inhibitor for use, a method, a use or a kit according to the invention, wherein the therapeutic agent is a recombinant fusion protein comprised of a human monoclonal antibody directed against fibroblast activation protein-alpha (FAP) linked to an engineered variant form of interleukin-2 (IL-2v);

A cathepsin S inhibitor for use, a method, a use or a kit according to the invention, wherein the therapeutic agent is cergutuzumab amunaleukin;

A cathepsin S inhibitor for use, a method, a use or a kit according to the invention, wherein the therapeutic agent is an anti-TNFalpha antibody;

A cathepsin S inhibitor for use, a method, a use or a kit according to the invention, wherein the therapeutic agent is infliximab (REMICADE®) or adalimumab (HUMIRA®);

A cathepsin S inhibitor for use, a method, a use or a kit according to the invention, wherein the cathepsin S inhibitor is (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylicacid(1-cyano-cyclopropyl)-amide; or (2S,4R)-4-[4-(5-methyl-tetrazol-2-yl)-2-trifluoromethyl-benzenesulfonyl]-1-(1-trifluoromethyl-cyclopropanecarbonyl)-pyrrolidine-2-carboxylicacid(1-cyano-cyclopropyl)-amide;

or a pharmaceutically acceptable salt thereof;

A cathepsin S inhibitor for use, a method, a use or a kit according to the invention, wherein the cathepsin S inhibitor is (2 S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof;

A cathepsin S inhibitor for use, a method, a use or a kit according to the invention, wherein the cathepsin S inhibitor is (2S,4R)-4-[4-(5-methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof;

A cathepsin S inhibitor for use, a method, a use or a kit according to the invention, wherein the cathepsin S inhibitor is (2 S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof and the therapeutic agent is infliximab (REMICADE®);

A cathepsin S inhibitor for use, a method, a use or a kit according to the invention, wherein the cathepsin S inhibitor is (2S,4R)-4-[4-(5-methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof and the therapeutic agent is infliximab (REMICADE®);

A cathepsin S inhibitor for use, a method, a use or a kit according to the invention, wherein the cathepsin S inhibitor is (2 S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof and the therapeutic agent is adalimumab (HUMIRA®);

A cathepsin S inhibitor for use, a method, a use or a kit according to the invention, wherein the cathepsin S inhibitor is (2S,4R)-4-[4-(5-methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof and the therapeutic agent is adalimumab (HUMIRA®);

A cathepsin S inhibitor for use, a method, a use or a kit according to the invention, wherein the cathepsin S inhibitor is (2 S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof and the therapeutic agent is cergutuzumab amunaleukin;

A cathepsin S inhibitor for use, a method, a use or a kit according to the invention, wherein the cathepsin S inhibitor is (2S,4R)-4-[4-(5-methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof and the therapeutic agent is cergutuzumab amunaleukin;

A cathepsin S inhibitor for use, a method, a use or a kit according to the invention, wherein the cathepsin S inhibitor is (2 S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof and the therapeutic agent is CEA-TCB;

A cathepsin S inhibitor for use, a method, a use or a kit according to the invention, wherein the cathepsin S inhibitor is (2S,4R)-4-[4-(5-methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof and the therapeutic agent is CEA-TCB;

A cathepsin S inhibitor for use, a method, a use or a kit according to the invention, wherein the cathepsin S inhibitor is (2 S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof and the therapeutic agent is FAP-OX40;

A cathepsin S inhibitor for use, a method, a use or a kit according to the invention, wherein the cathepsin S inhibitor is (2S,4R)-4-[4-(5-methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof and the therapeutic agent is FAP-OX40;

A cathepsin S inhibitor for use, a method, a use or a kit according to the invention, wherein the cathepsin S inhibitor is (2 S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof and the therapeutic agent is atezolizumab;

A cathepsin S inhibitor for use, a method, a use or a kit according to the invention, wherein the cathepsin S inhibitor is (2S,4R)-4-[4-(5-methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof and the therapeutic agent is atezolizumab;

A cathepsin S inhibitor for use, a method, a use or a kit according to the invention, wherein the cathepsin S inhibitor is (2 S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof and the therapeutic agent is CEA-TCB in combination with atezolizumab;

A cathepsin S inhibitor for use, a method, a use or a kit according to the invention, wherein the cathepsin S inhibitor is (2S,4R)-4-[4-(5-methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof and the therapeutic agent is CEA-TCB in combination with atezolizumab;

A cathepsin S inhibitor for use, a method, a use or a kit according to the invention, wherein the cathepsin S inhibitor is administered in an amount that is sufficient to reduce or prevent the formation of ADA against the therapeutic agent;

A cathepsin S inhibitor for use, a method, a use or a kit according to the invention, wherein the cathepsin S inhibitor is administered at dose of between 50 mg/kg/day and 400 mg/kg/day, in particular between 75 mg/kg/day and 250 mg/kg/day, more particularly at 100 mg/kg/day or 200 mg/kg/day; and A cathepsin S inhibitor for use, a method, a use or a kit according to the invention, wherein the cathepsin S inhibitor is administered at dose of 200 mg/kg/day, in particular 100 mg/kg b.i.d.;

A cathepsin S inhibitor for use, a method, a use or a kit according to the invention, wherein the cathepsin S inhibitor is administered at dose of 200 mg/kg/day, in particular 100 mg/kg b.i.d. and wherein the cathepsin S inhibitor is (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof; and A cathepsin S inhibitor for use, a method, a use or a kit according to the invention, wherein the cathepsin S inhibitor is administered at dose of 200 mg/kg/day, in particular 100 mg/kg b.i.d. and wherein the cathepsin S inhibitor is (2S,4R)-4-[4-(5-methyl-tetrazol-2-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide or a pharmaceutically acceptable salt thereof.

The above doses are given for the free base. If a salt is administered, the dose shall be adapted so that in the end the above doses of free base are available to the patient.

In the cathepsin S inhibitor for use in the treatment of IBD, the patient is advantageously receiving a treatment with a therapeutic agent selected from an anti-TNFalpha antibody like infliximab or adalimumab, an anti-α4β7 integrin antibody like vedolizumab, an anti-p40 antibody like ustekinumab, a JAK1 or JAK3i inhibitor like tofacitinib or an anti-1123 antibody like risankizumab, more particularly an anti-TNFalpha antibody like infliximab or adalimumab.

In the method of treatment of IBD, comprising administering a cathepsin S inhibitor to a patient in need thereof, the patient is advantageously receiving a treatment with a therapeutic agent selected from an anti-TNFalpha antibody like infliximab or adalimumab, an anti-α4β7 integrin antibody like vedolizumab, an anti-p40 antibody like ustekinumab, a JAK1 or JAK3i inhibitor like tofacitinib or an anti-IL23 antibody like risankizumab, more particularly an anti-TNFalpha antibody like infliximab or adalimumab.

The invention will now be illustrated by the following examples which have no limiting character.

EXAMPLES

Example 1: Mitigation of ADA Against HUMIRA® (Adalimumab) and CEA-IL2v (28 Days)

Adalimumab and CEA-IL2v are known to be immunogenic in the clinic (Bartelds, Krieckaert et al. JAMA 2011, 305(14): 1460-1468, van Schouwenburg, Rispens et al. Nat Rev Rheumatol 2013, 9(3): 164-172).

Adalimumab is an anti-TNFα inhibiting antibody shown to be highly immunogenic in mice.

In contrast, CEA-IL2v is an immunomodulatory drug for oncology indication.

For immunogenicity assessment, we used the previously described human IgG1 immune-tolerant mouse model (Bessa, Boeckle et al. Pharm Res 2015, 32(7): 2344-2359). Since this human IgG transgenic mouse is tolerant to a broad range of human IgG1 antibodies (Abs), ADA responses elicited in this system are taken to reflect intrinsic immunogenic attributes of the eliciting Ab compounds also expected to cause ADA in humans.

(2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide is a cathepsin S inhibitor known to inhibit WWII maturation and antigen presentation by antigen-presenting cells (WO 2010/121918; Theron, Bentley et al. 2017, Front Immunol 8: 806). It is used in the experiments below.

Immunization 15-week-old mice C57BL/6 wild type and C57BL/6-Tg (hIgG1,k,l) were purchased from Taconic (Denmark) and housed at the animal facilities under a 12 hour (h) light 12 h dark cycle with cycles of air ventilation and free access to water and food. 7×10 μg of CEA-112v or 7×10 μg of Humira (Adalimumab, Abbvie Germany GmbH) were injected respectively at day 0, 4, 7, 11, 14, 18 and 21 subcutaneously in the right flank or the left flank alternatively. The dosage of the cathepsin S inhibitor consumption was 40 mg/kg/day. The food admix (Ssniff Spezialdiäten, Germany) was given daily one day before the first immunization until day 28 for the mice immunized with Humira. The food admix was given daily one week before the first immunization until day 28 for the mice immunized with CEA-IL2v (R06895882). At day −12, 7, 14 and 28 blood samples were taken.

ADA Measurement

Nunc Maxisorp flat-bottom 96 well ELISA plates were coated with 100 μl per well of Humira or CEA-PGLALA (3.42 mg/ml, ID 8037) respectively at 5 μg/mL in NaHCO$_3$100 mM buffer overnight at +4° C. The next day the ELISA plates were washed 3 times with PBS+0.05% Tween. For blocking, 100 μl of PBS+2% BSA were added to each well and the ELISA plates were incubated 2 hours at room temperature. The sera were diluted 1 to 50 in PBS+1% FBS in the first raw of round bottom dilution plate, following by a 1 to 3 serial dilution step, 7 times in PBS+1% FBS. The ELISA plates were washed 3 times with PBS+0.05% Tween and 100 μl of the diluted sera were transferred from the dilution plate to the ELISA plate. After 2 hours of incubation at room temperature, the ELISA plates were washed 3 times with PBS+0.05% Tween. For detection of ADA, 100 μl per well of goat anti mouse IgG Alkaline Phosphatase conjugated (Jackson Cat no 115-055-071) diluted 1:2000 in PBS+1% BSA were added. After 1 hour of incubation at room temperature, the ELISA plates were washed 3 times with PBS+0.05% Tween. 100 μl of substrate P-nitrophenyl phosphate ready to use (Life Technologies Cat no 002212) were added per well and after 10 min incubation at room temperature, the OD at 405 nm was read as an end-point measurement with a Versamax ELISA reader.

The results are shown in FIGS. 1-2.

These results show that animals fed with a cathepsin S inhibitor and immunized with adalimumab showed reduced ADA levels compared to vehicle treated animals (FIG. 1). Interestingly, the effect was more pronounced at later timepoints and at higher serum dilutions, suggesting that either the cathepsin S inhibitor has a preferential effect in inhibiting the late emerging high affinity antibody responses or that one day prior immunization was not sufficient to prevent a certain degree of antigen presentation by APCs.

Figure 2A:
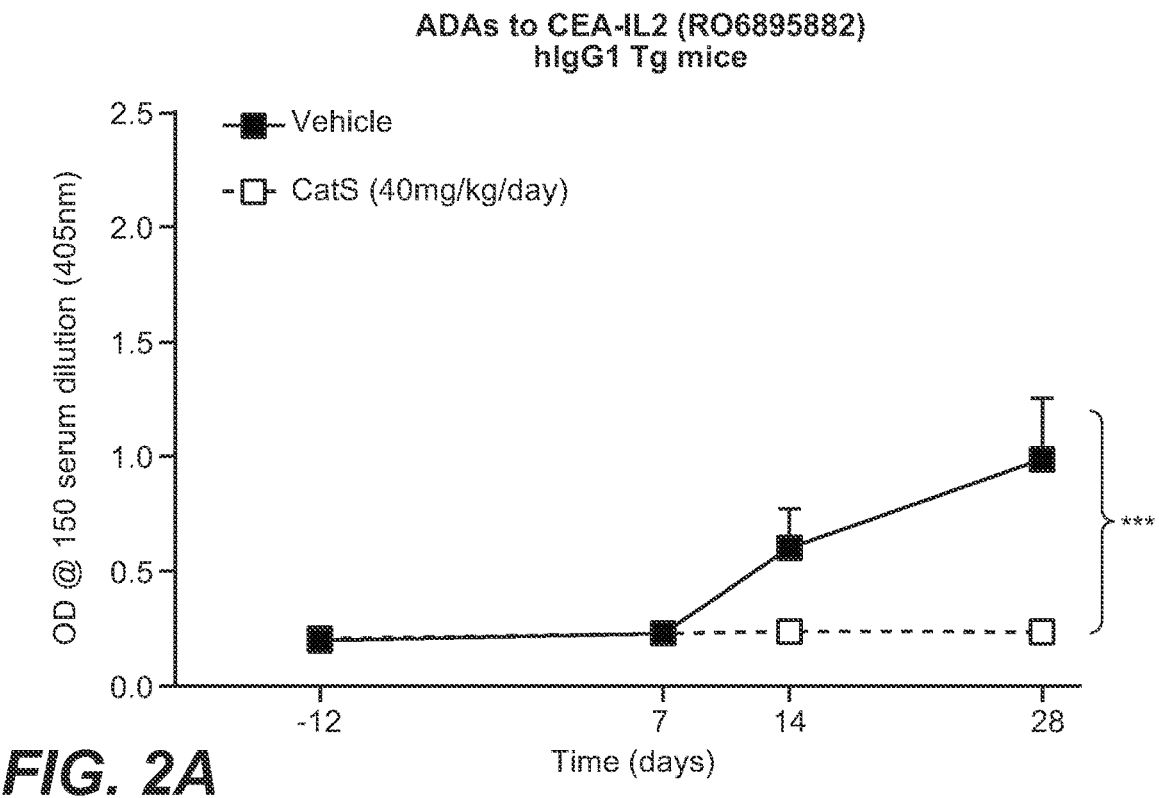
Figure 2B:
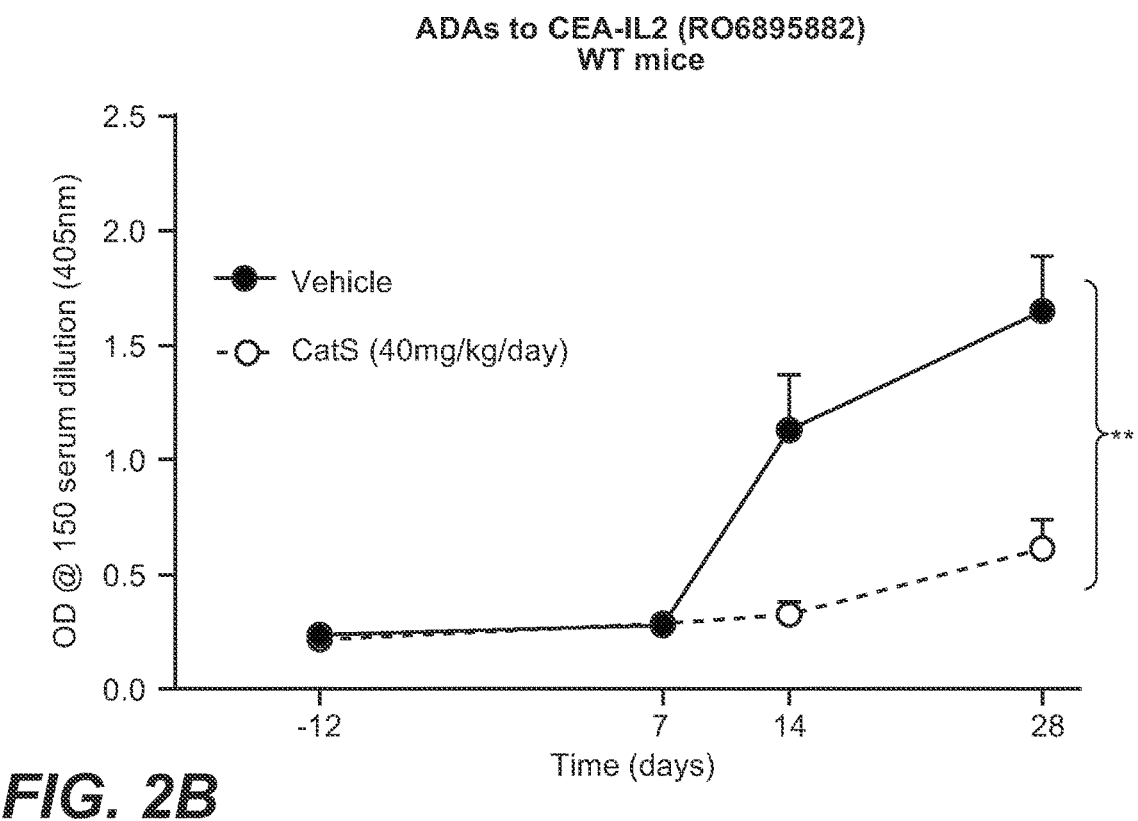

Our experiments also revealed that prophylactic treatment with a cathepsin S inhibitor (7 days prior immunization) lead to complete abrogation of ADA to CEA-IL2v in hIgG transgenic mice (FIG. 2A). In contrast, only partial reduction of ADA was achieved in wild-type (WT) mice (FIG. 2B). This is likely explained by the overall higher magnitude of ADA induced in WT animals (anti-Fc and anti-idiotypic ADA) in comparison to hIgG Tg mice (only anti-idiotypic ADA).

Example 2: Abrogation of T-Cell Dependent IgG Response

Immunization by NP-OVAL 6 to 8-weeks-old female mice C57BL/6-Tg (hIgG1,k,l) were purchased from Charles River Laboratories (Germany) and housed at the animal facilities in room with air-conditioned under a 12 hours light/dark cycle in macrolon boxes with enriched environment and free access to water and food. The mice were injected at day −2 subcutaneously with 20 μg/mouse of NP-OVAL (4-Hydroxy-3-nitrophenylacetyl hapten conjugated to ovalbumin, Biosearch Technologies, USA, Batch No 060368) with adjuvant (Alhydrogel, InvivoGen #vac-alu-250) at the both flanks or without adjuvant at day 28. The dosage of (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide consumption was 0 (vehicle), 1, 10, 40 mg/kg/day. The cathepsin S antagonist (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide was given via food admix (Ssniff Spezialdiäten, Germany) daily from two days before the first NP-OVAL immunization until day 35. At day −2, 1, 7, 12, 21, 28 and 35 blood samples from the tail were taken in BD Microtainer tubes SST. After 30 min of resting the tubes were centrifuged at 10'000 g for 10 min and stored at −20° C.

NP Specific IgG Measurement

Nunc Maxisorp flat-bottom 96 well ELISA plates were coated with 100 µl per well of NP(4)-BSA (Biosearch Technologies N-5050L; 1 mg/mL) at 1 µg/mL in NaHCO$_3$100 mM buffer and incubated overnight at +4° C. The next day the ELISA plates were washed 3 times with PBS+0.05% Tween. For blocking, 100 µl of PBS+2% BSA were added to each well and the ELISA plates were incubated 2 hours at room temperature. The sera were diluted 1 to 50 in PBS+1% FBS in the first raw of round bottom dilution plate, following by a 1 to 3 serial dilution step, 7 times in PBS+1% FBS. The ELISA plates were washed 3 times with PBS+0.05% Tween and 100 µl of the diluted sera were transferred from the dilution plate to the ELISA plate. After 2 hours of incubation at room temperature, the ELISA plates were washed 3 times with PBS+0.05% Tween. For detection of NP specific IgG, 100 µl per well of goat anti mouse IgG Alkaline Phosphatase conjugated (Jackson Cat no 115-055-071) diluted 1:2000 in PBS+1% BSA were added. After 1 hour of incubation at room temperature, the ELISA plates were washed 3 times with PBS+0.05% Tween. 100 µl of substrate P-nitrophenyl phosphate ready to use (Life Technologies, Cat no 002212) were added per well and after 10 min incubation at room temperature, the OD at 405 nm was read as an end-point measurement with a Versamax ELISA reader.

Figure 3:
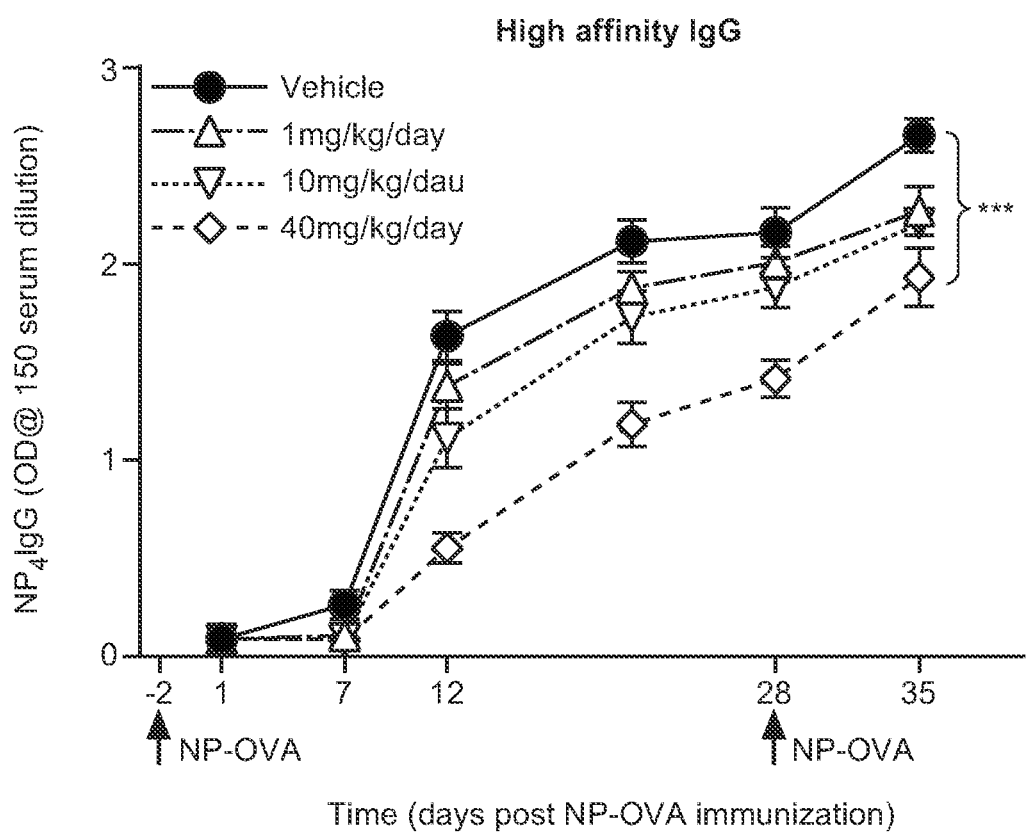

The results are shown in FIG. 3.

The dose of 40 mg/kg/day of the cathepsin S antagonist was capable of effectively abrogating the T-cell dependent IgG response against NP.

Example 3: Mitigation of ADA Against HUMIRA® (Adalimumab) (63 Days)

Immunization 15-week-old female mice C57BL/6-Tg (hIgG1,k,l) were purchased from Taconic (Denmark) and housed at the animal facilities in room with air-conditioned under a 12 hours light/dark cycle in macrolon boxes with enriched environment and free access to water and food. 7×10 µg of Humira (Adalimumab, Abbvie Germany GmbH) were injected at day 0, 4, 7, 11, 14, 18 and 21 subcutaneously in the right flank or the left flank alternatively. The dosage of (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide consumption was 40 mg/kg/day. (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide was given via food admix (Ssniff Spezialdiäten, Germany) daily from one day before the first Humira immunization until day 28. At day −4, 7, 14, 21, 28, 42, 49 and 56 blood samples from the tail were taken in BD Microtainer tubes SST before dosing. After 30 min of resting the tubes were centrifuged at 10'000 g for 10 min and stored at −20° C.

ADA Measurement

Nunc Maxisorp flat-bottom 96 well ELISA plates were coated with 100 µl per well of Humira or CEA-PGLALA respectively at 5 µg/mL in NaHCO$_3$100 mM buffer overnight at +4° C. The next day the ELISA plates were washed 3 times with PBS+0.05% Tween. For blocking, 100 µl of PBS+2% BSA were added to each well and the ELISA plates were incubated 2 hours at room temperature. The sera were diluted 1 to 50 in PBS+1% FBS in the first raw of round bottom dilution plate, following by a 1 to 3 serial dilution step, 7 times in PBS+1% FBS. The ELISA plates were washed 3 times with PBS+0.05% Tween and 100 µl of the diluted sera were transferred from the dilution plate to the ELISA plate. After 2 hours of incubation at room temperature, the ELISA plates were washed 3 times with PBS+0.05% Tween. For detection of ADAs, 100 µl per well of goat anti mouse IgG Alkaline Phosphatase conjugated (Jackson Cat no 115-055-071) diluted 1:2000 in PBS+1% BSA were added. After 1 hour of incubation at room temperature, the ELISA plates were washed 3 times with PBS+0.05% Tween. 100 µl of substrate P-nitrophenyl phosphate ready to use (Life Technologies, Cat no 002212) were added per well and after 10 min incubation at room temperature, the OD at 405 nm was read as an end-point measurement with a Versamax ELISA reader.

Figure 4:
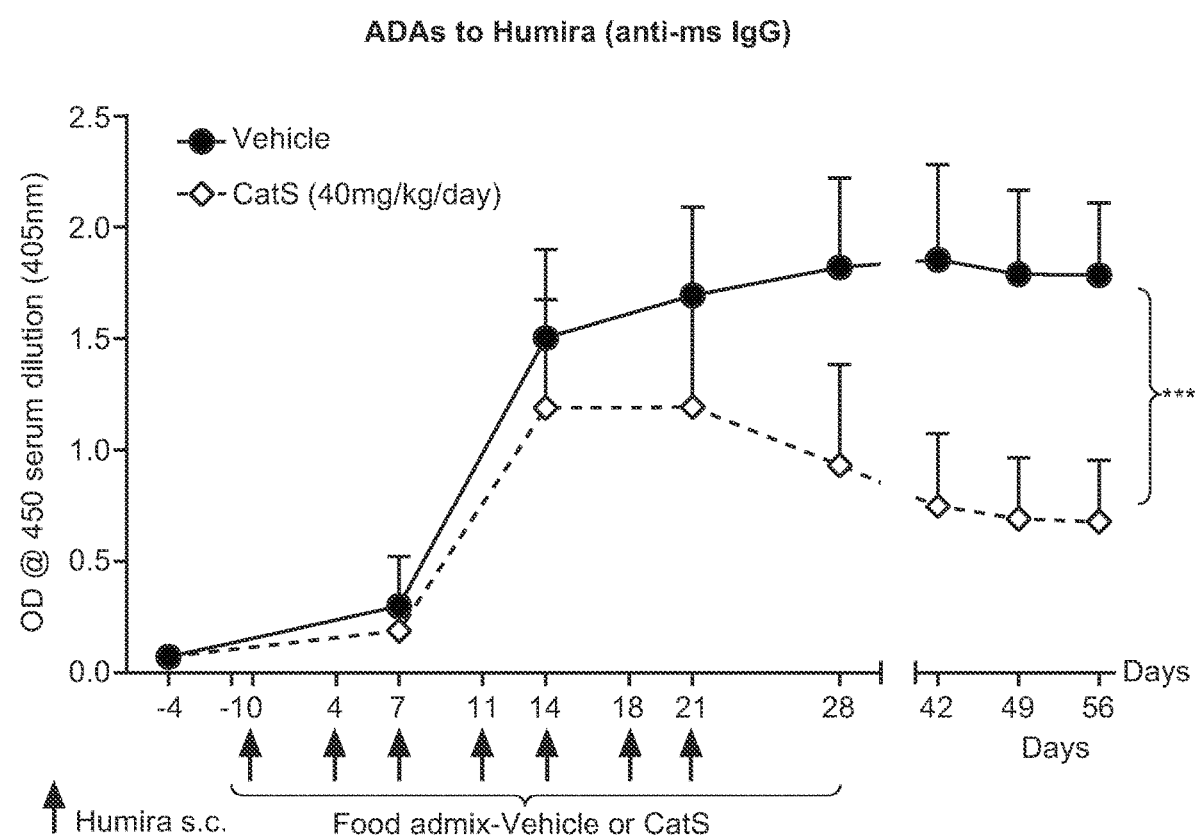

The results are shown in FIG. 4.

Example 4: Mitigation of ADA Against CEA-IL2v (63 Days)

Immunization 15-week-old mice C57BL/6-Tg (hIgG1,k,l) and C57BL/6 wild type mixed gender were purchased from Taconic (Denmark) and housed at the animal facilities in room with air-conditioned under a 12 hours light/dark cycle in macrolon boxes with enriched environment and free access to water and food. 7×10 µg of CEA-IL2v (Batch no GLI0144-01) were injected at day 0, 4, 7, 11, 14, 18 and 21 for the primary response, and at day 49, 53, 56 and 60 for the memory response. The CEA-112v injections were done subcutaneously in the right flank or the left flank alternatively. The dosage of (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide consumption was 40 mg/kg/day. (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide was given via food admix (Ssniff Spezialdiäten, Germany) daily from one week before the first CEA-IL2v immunization until day 28 for the primary response and from day 42 (one week before boost with CEA-112v) until day 78 for the memory response. At day −12, 7, 14, 28, 42, 56 and 63 blood samples from the tail were taken before dosing. For serum and PK samples Sarstedt Micro tubes 1, 1 ml Z gel (cat. no 41.1378.005) were used. After 30 min of resting the tubes were centrifuged at 10,000 g for 10 min and stored at −20° C. For PD samples Sarstedt Microvette® 100 Lithium-Heparin tubes (cat. no 20.1282) were used and kept at room temperature until measurement the same day.

ADA Measurement

Nunc Maxisorp flat-bottom 96 well ELISA plates were coated with 100 µl per well of Humira or CEA-PGLALA respectively at 5 µg/mL in NaHCO$_3$100 mM buffer overnight at +4° C. The next day the ELISA plates were washed 3 times with PBS+0.05% Tween. For blocking, 100 µl of PBS+2% BSA were added to each well and the ELISA plates were incubated 2 hours at room temperature. The sera were diluted 1 to 50 in PBS+1% FBS in the first raw of round bottom dilution plate, following by a 1 to 3 serial dilution step, 7 times in PBS+1% FBS. The ELISA plates were washed 3 times with PBS+0.05% Tween and 100 µl of the diluted sera were transferred from the dilution plate to the ELISA plate. After 2 hours of incubation at room temperature, the ELISA plates were washed 3 times with PBS+0.05% Tween. For detection of ADAs, 100 µl per well of goat anti mouse IgG Alkaline Phosphatase conjugated (Jackson Cat no 115-055-071) diluted 1:2000 in PBS+1% BSA were added. After 1 hour of incubation at room temperature, the ELISA plates were washed 3 times with PBS+0.05% Tween. 100 µl of substrate P-nitrophenyl phosphate ready to use (Life Technologies, Cat no 002212) were added per well and after 10 min incubation at room temperature, the OD at 405 nm was read as an end-point measurement with a Versamax ELISA reader.

Figure 5A:
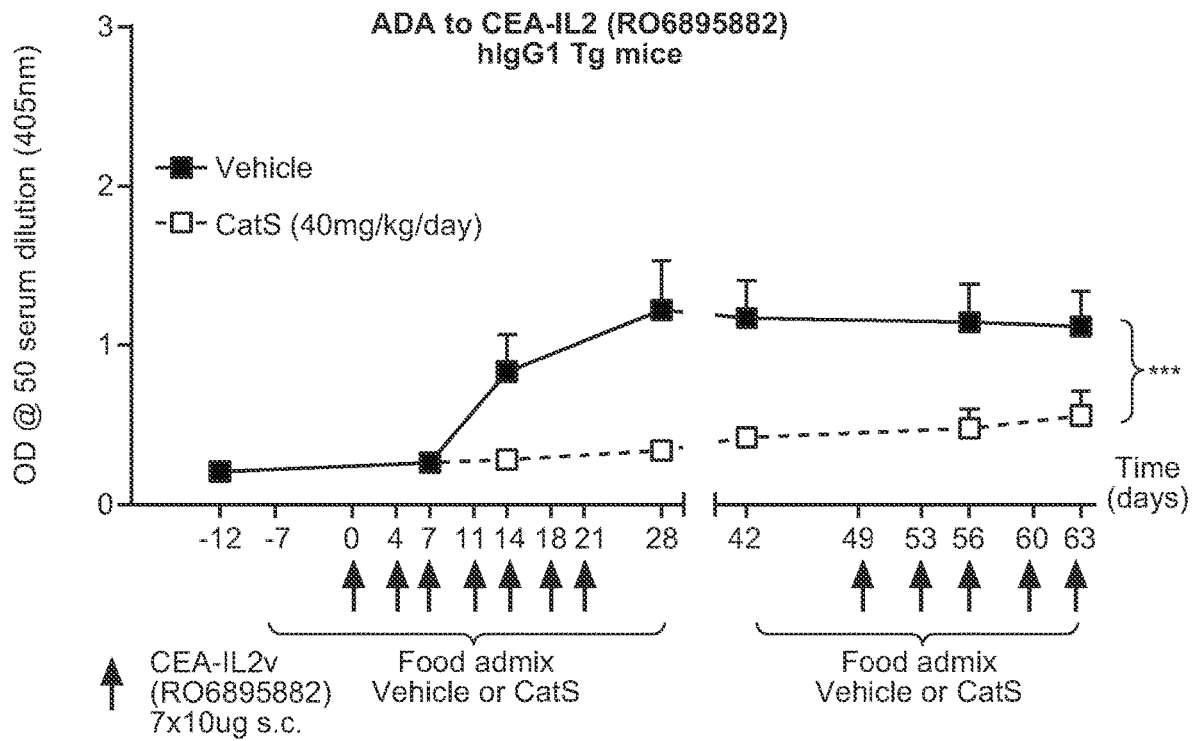
Figure 5B:
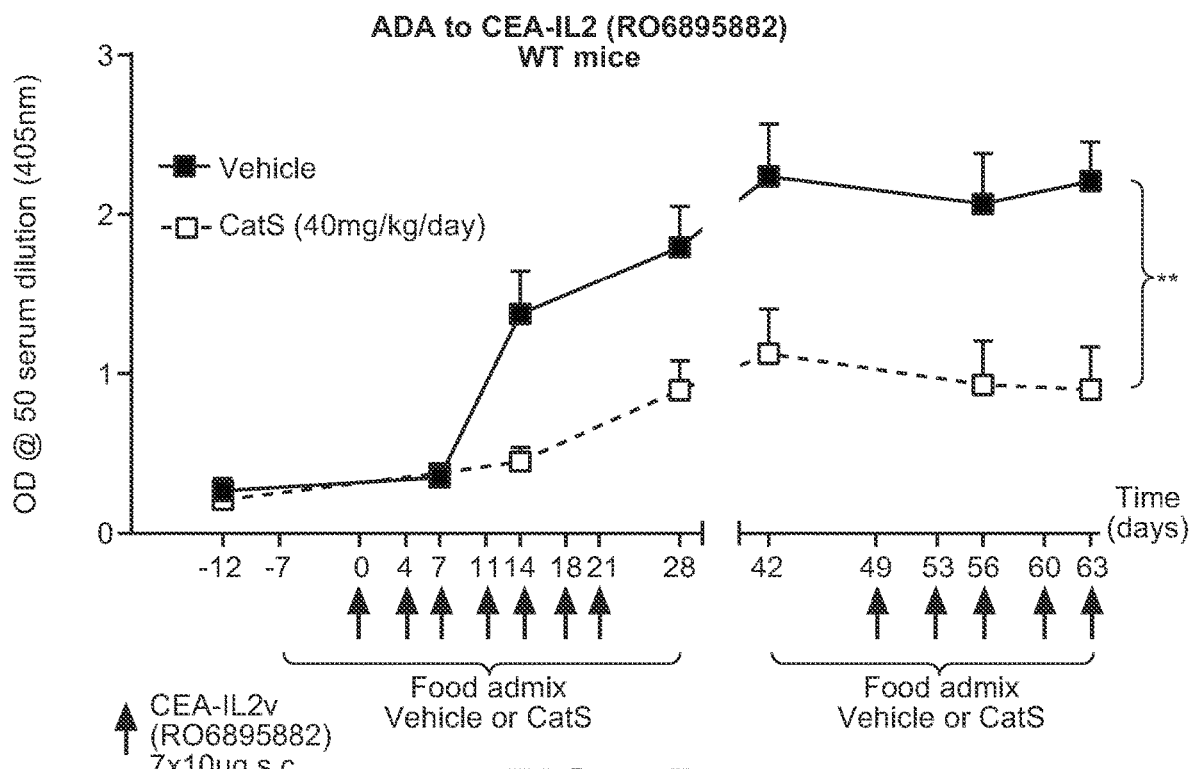

The results are shown in FIGS. 5A and 5B.

Example 5: CEA-IL2v Exposure in Tg and Wild-Type Mices

PK Measurement

Serum samples from C56BL/6 hIgG tg and wildtype mice treated with CEA-IL2v (Example 4) were analysed using an enzyme-linked immunosorbent assay (ELISA) under non-GLP conditions. For the ELISA method capture antibody (mAb<CEA>M-Bi), calibrators (R06895882), diluted serum samples, detection antibody (mAb<CEA>M-Dig) and anti-digoxigenin-POD are added successively to a streptavidin coated microtiter plate (SA-MTP). Formed immobilized immune complexes are detected by addition of the substrate solution ABTS. The color intensity was determined photometrically and was proportional to the analyte concentration in the test sample.

Figure 6A:
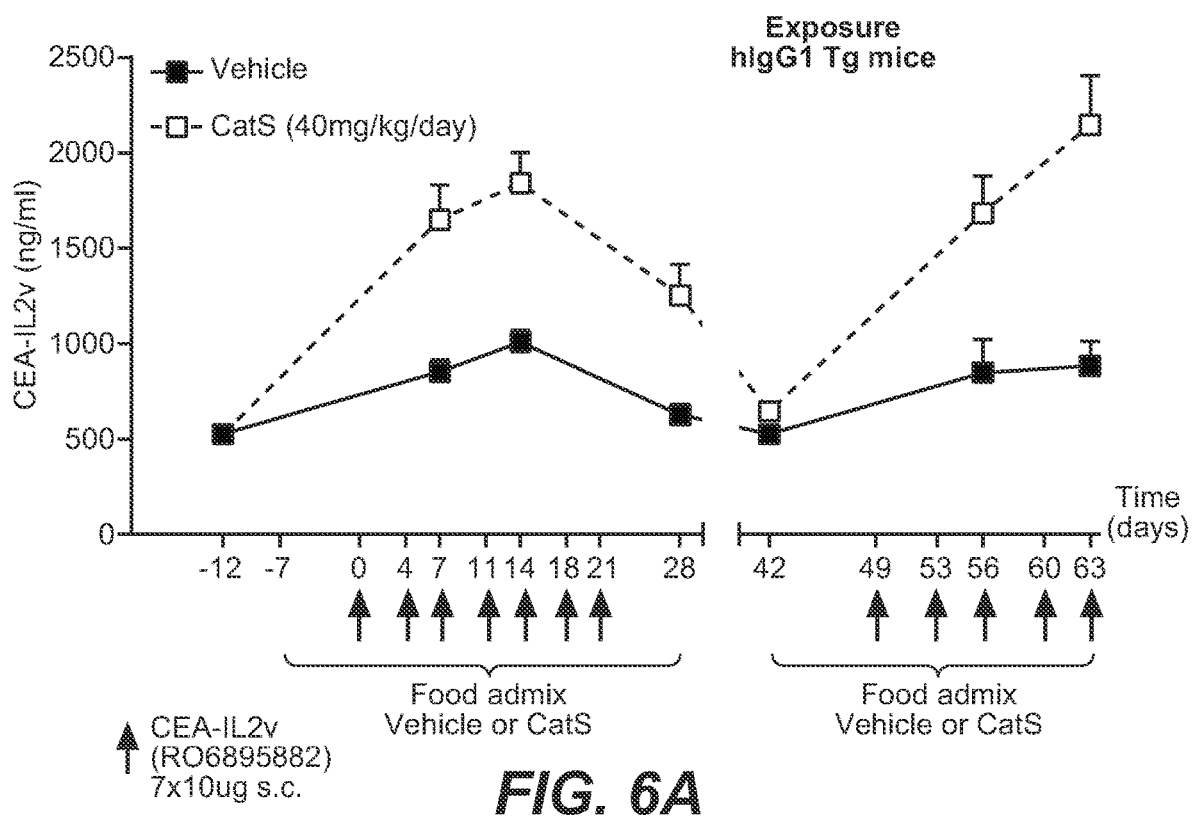
Figure 6B:
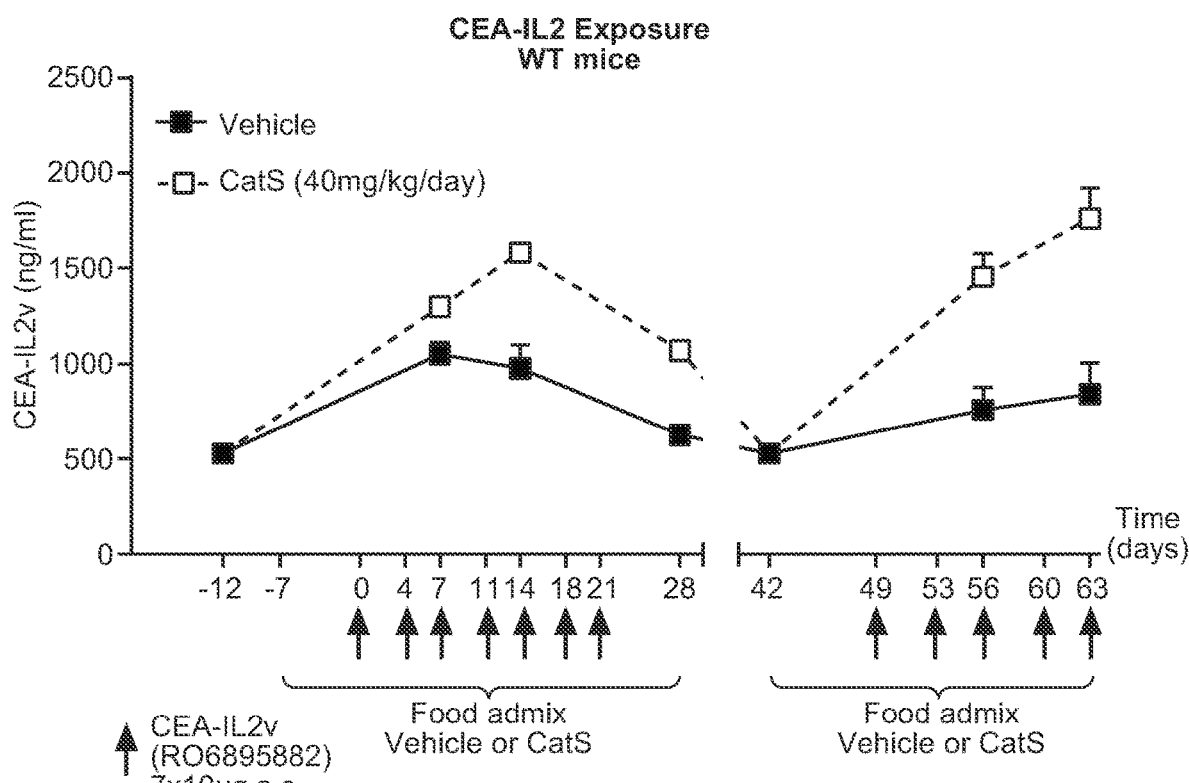
Figure 7A:
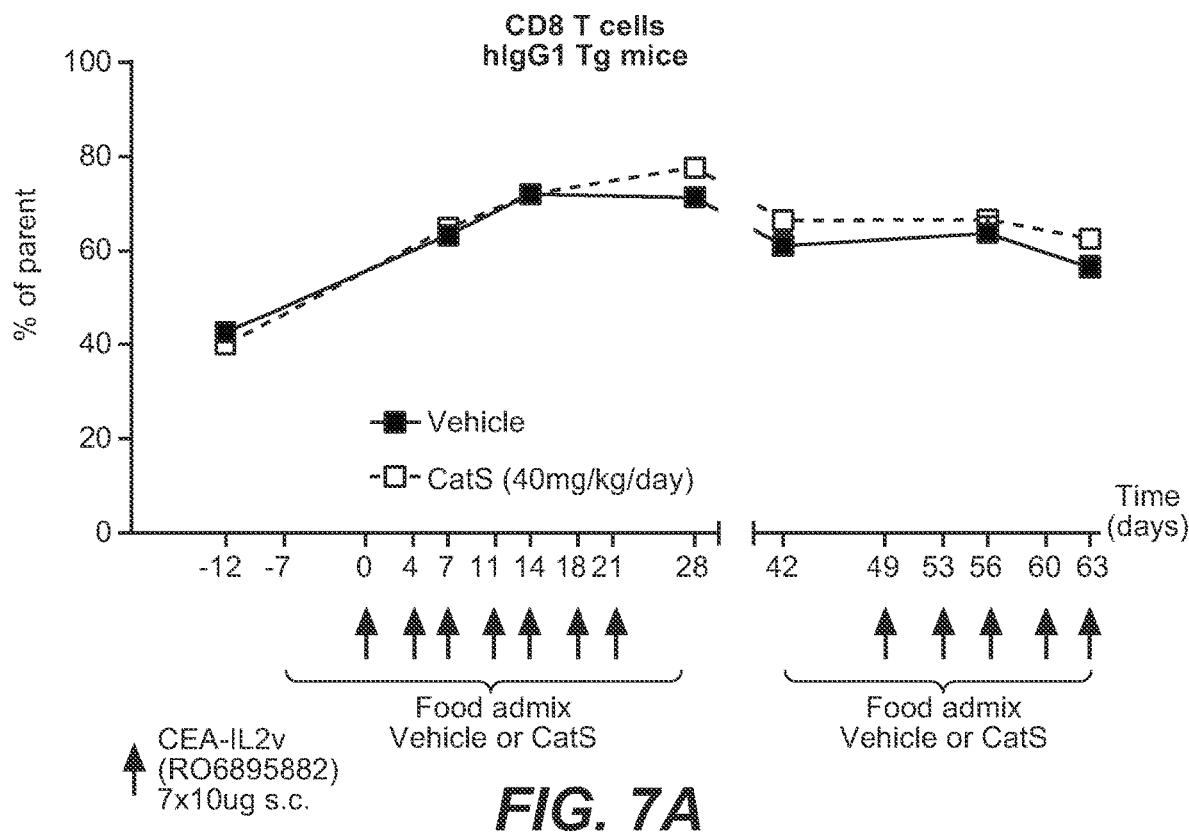
Figure 7B:
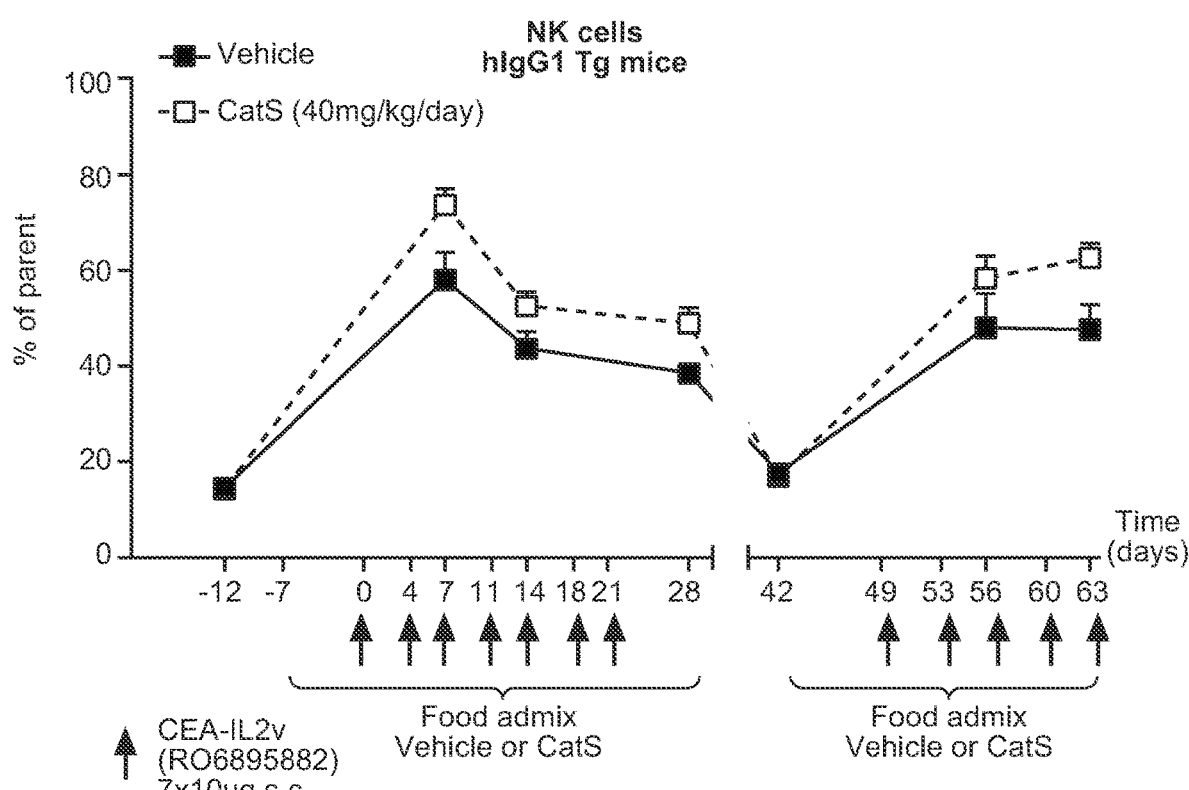
Figure 7C:
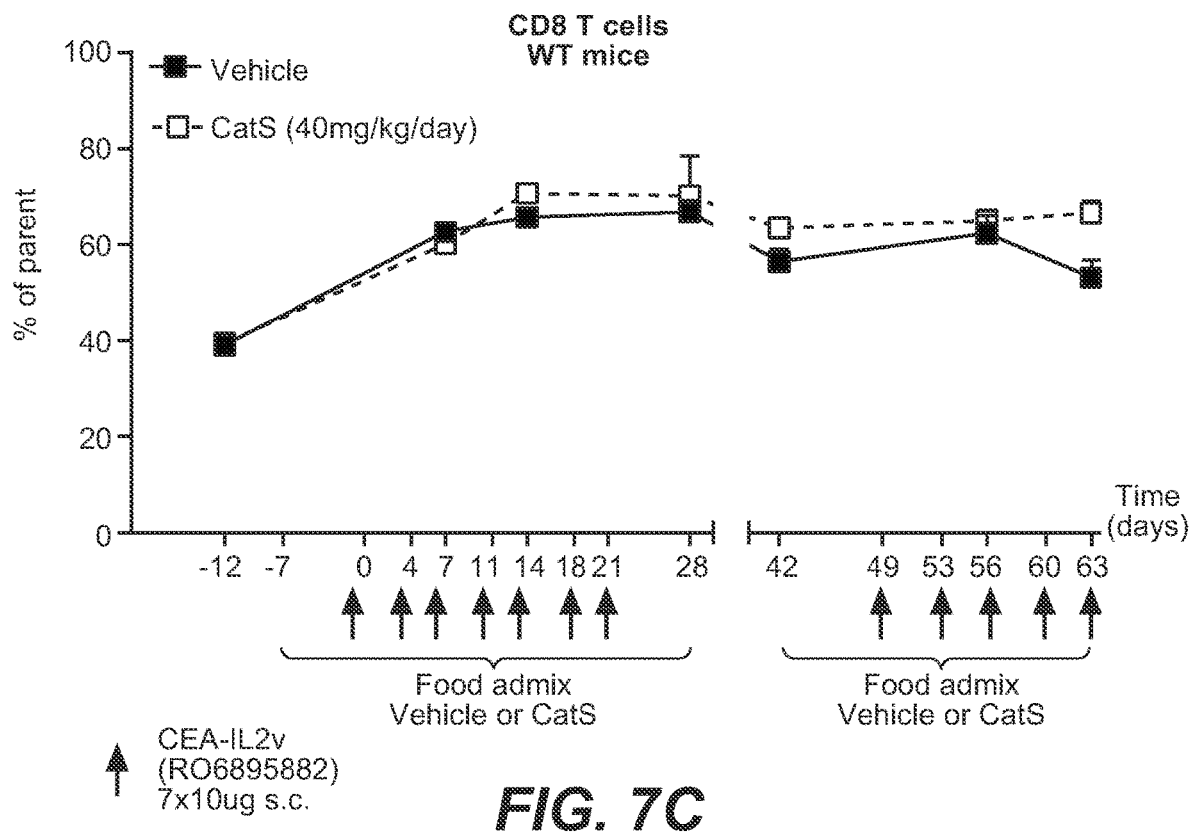
Figure 7D:
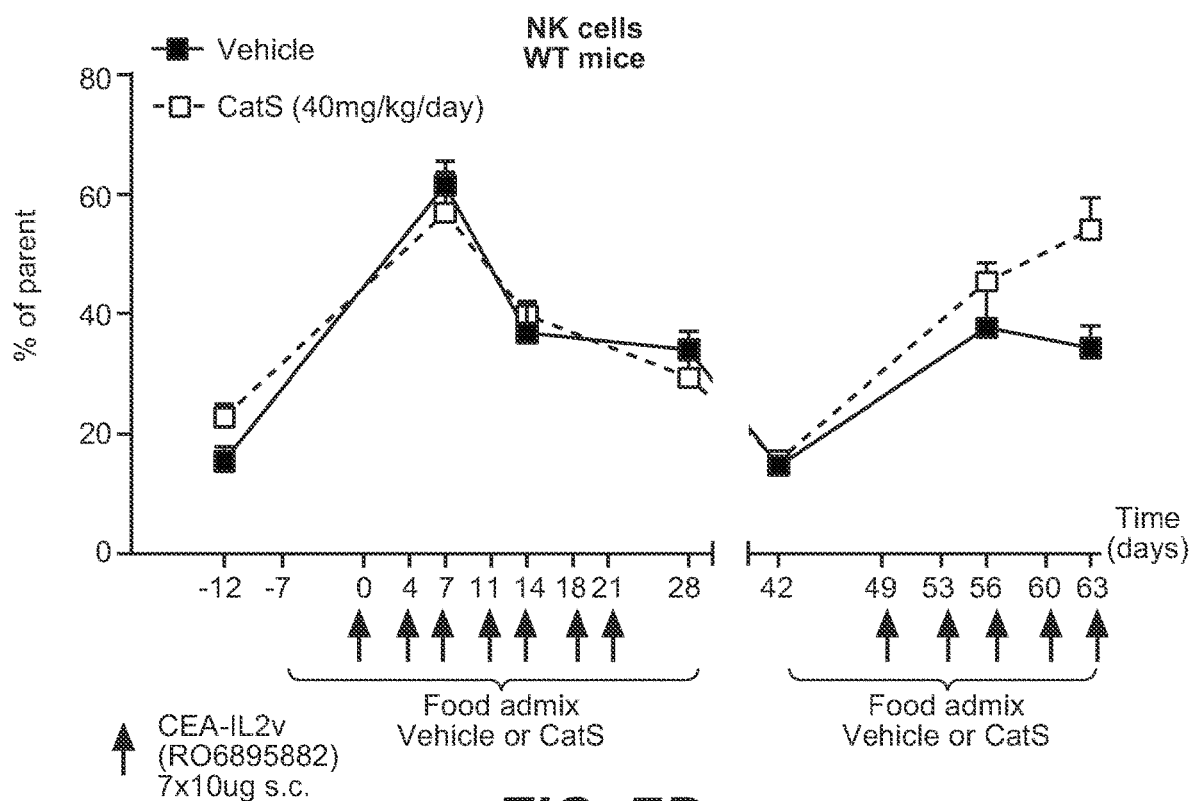

The results are shown in FIGS. 6A and 6B.

The cathepsin S inhibitor significantly increases and prolongs CEA-112v exposure.

PD Measurement

From Example 4, 50 µl of lithium heparin whole blood were transferred into a 5 ml polystyrene round-bottom tubes (BD Falcon, Cat. no 352058) and 2 ml of freshly prepared 1× Pharm Lyse™ lysing buffer (BD Bioscience, Cat. no 555899) with UltraPur™ distilled water (Invitrogen, Cat. no 10977-035) were added. The samples were vortexed thoroughly and incubated for 15 min at room temperature. After the incubation time, the tubes were spin down at 300 g for 5 min, the supernatants were removed and the cells pellets were washed with 2 ml DPBS (Gibco, Cat. no 14190-094)+2% Fetal bovine serum (Gibco, Cat. no 10082147). The tubes were spin down at 300 g for 5 min and the supernatants were removed. 100 µl of TruStain fcX™ (BioLegend, Cat. no 101320) diluted at 1:100 in DPBS+2% FBS were added to the cell pellets, carefully vortexed and incubated for 15 at room temperature. A master mix was prepared with 0.5 µl of BV510-conjugated anti mouse CD45 (Biolegend, Cat. no 103138), 0.4 µl of PE-Cy5-conjugated anti mouse TCRb (Biolegend, Cat. no 109210), 0.5 µl of BUV737-conjugated anti mouse CD4 (BD Biosciences, Cat. no 564298), 0.5 µl of BUV395-conjugated anti mouse CD8 (BD Biosciences, Cat. no 563786), 0.5 µl of BV605-conjugated anti mouse NKP46 (BD Biosciences, Cat. no 564069), and 0.5 µl of BV605-conjugated anti mouse NK1.1 (Biolegend, Cat. no 108740) per sample. 3 µl of the master mix were added to the samples. After 30 min of incubation at +4° C. in the dark, 2 ml of DPBS+2% FBS were added and the tubes were spin down at 300 g, +4° C. The supernatants were removed and the pellets were re-suspend with 150 µl of DPBS+2% FBS. Data were acquired with the BD FACSDiva software v8.0 on BD LSRFortessa™ cytometer and analyzed with FlowJo™ V10.

The results are shown in FIGS. 7A-7D.

CEA-112v pharmacology is preserved in cathepsin S inhibitor treated animals.

Example 6: Mitigation of ADA Against FAP-OX40

Immunization 10-week-old female mice C57BL/6 were purchased from Charles River Laboratories (Germany) and housed at the animal facilities in room with air-conditioned under a 12 hours light/dark cycle in macrolon boxes with enriched environment and free access to water and food. 12.5 mg/kg of muFAP-OX40iMab (P1AD4396-005) were injected at day 1, 4 and 8 intravenously to the group 2 (n=10 mice) and at day 1, 4, 8, 11, 15, 18 and 22 to the group 3 (n=10 mice) respectively. The dosage of (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide consumption was 40 mg/kg/day. (2 S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide was given via food admix (Ssniff Spezialdiäten, Germany) daily from one week before the first muFAP-OX40iMab immunization until day 23 to the group 3. The group 2 were feed with chow diet provided by Ssniff for the same time. At day −7, 8, 15, and 23 blood samples from the tail were taken in Sarstedt Micro tubes 1, 1 ml Z gel (cat. no 41.1378.005) before dosing. After 30 min of resting the tubes were centrifuged at 10'000 g for 10 min and stored at −20° C.

ADA Measurement

Nunc Maxisorp flat-bottom 96 well ELISA plates were coated with 100 µl per well of FAP(28H1)-OX40(49B4) PGLALA (P1AD4523) or anti OX40 moIgG2a (P1AD4561) respectively at 5 µg/mL in NaHCO$_3$100 mM buffer overnight at +4° C. The next day the ELISA plates were washed 3 times with PBS+0.05% Tween. For blocking, 100 µl of PBS+2% BSA were added to each well and the ELISA plates were incubated 2 hours at room temperature. The sera were diluted 1 to 50 in PBS+1% FBS in the first raw of round bottom dilution plate, following by a 1 to 3 serial dilution step, 7 times in PBS+1% FBS. The ELISA plates were washed 3 times with PBS+0.05% Tween and 100 µl of the diluted sera were transferred from the dilution plate to the ELISA plate. After 2 hours of incubation at room temperature, the ELISA plates were washed 3 times with PBS+0.05% Tween. For detection of ADAs, 100 µl per well of goat anti mouse IgG Alkaline Phosphatase conjugated (Jackson Cat no 115-055-071) diluted 1:2000 in PBS+1% BSA were added. After 1 hour of incubation at room temperature, the ELISA plates were washed 3 times with PBS+0.05% Tween. 100 µl of substrate P-nitrophenyl phosphate ready to use (Life Technologies, Cat no 002212) were added per well and after 10 min incubation at room temperature, the OD at 405 nm was read as an end-point measurement with a Versamax ELISA reader.

Figure 8A:
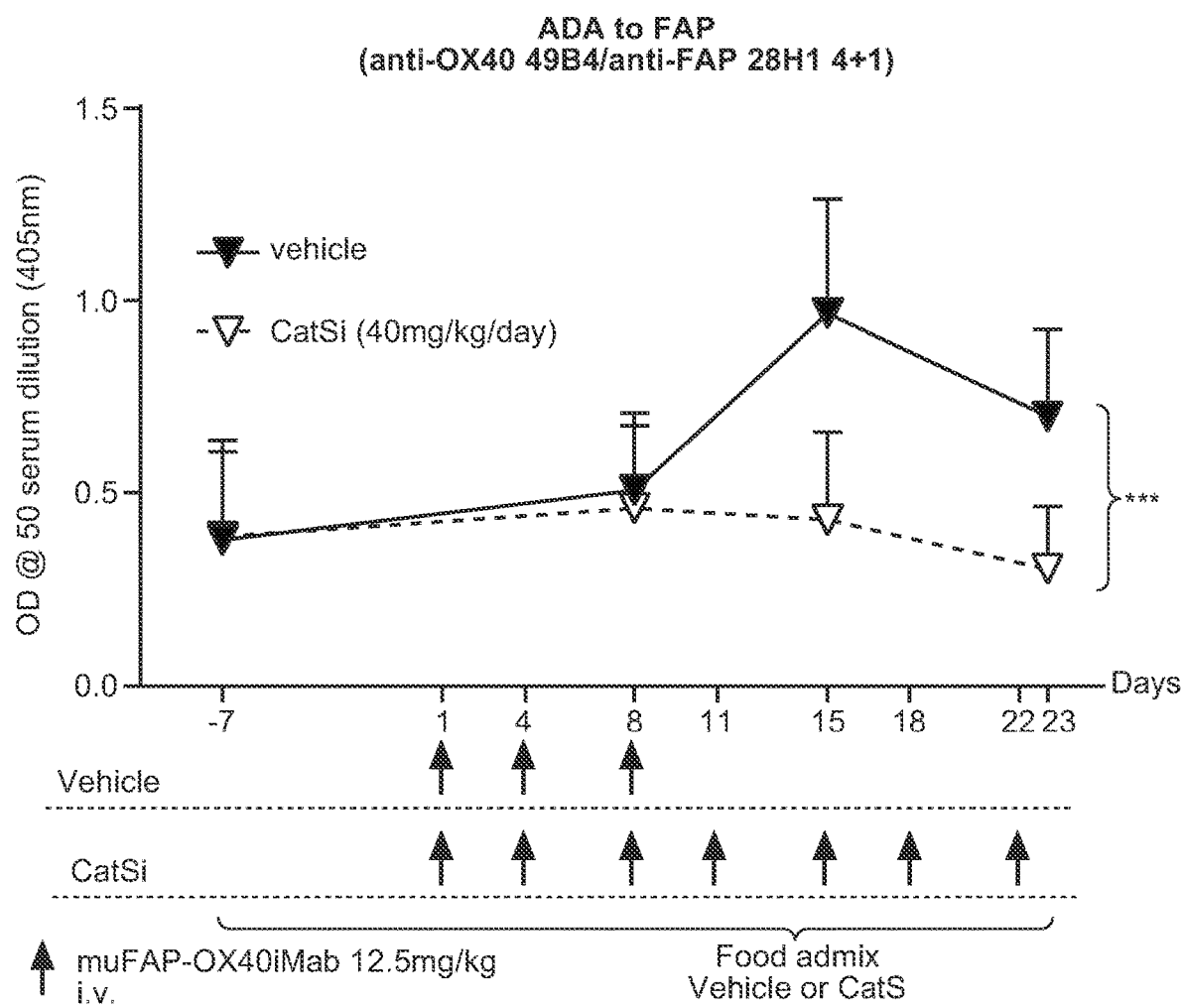
Figure 8B:
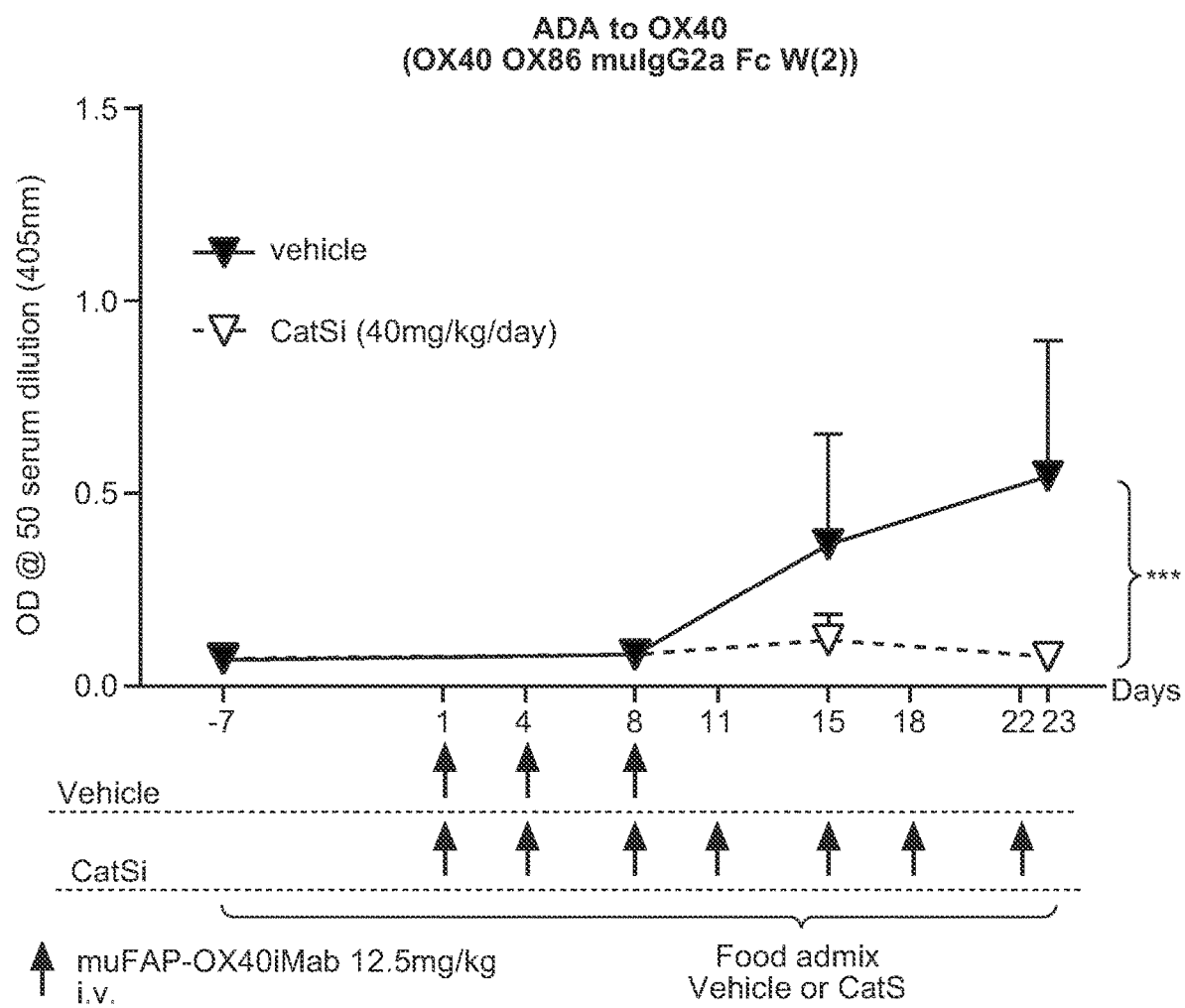

The results are shown in FIGS. 8A and 8B.

Example 7: Mitigation of ADA Against PD-L1

Immunization 10-week-old female mice C57BL/6 were purchased from Charles River Laboratories (Germany) and housed at the animal facilities in room with air-conditioned under a 12 hours light/dark cycle in macrolon boxes with enriched environment and free access to water and food. 10 mg/kg of muPD-L1 (P1AE4930-001) were injected at day 1, 8 and 15 intravenously to the group 4 (n=10 mice) and at day 1, 8, 15 and 22 to the group 5 (n=10 mice) respectively. The dosage of (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide consumption was 40 mg/kg/day. (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide was given via food admix (Ssniff Spezialdiäten, Germany) daily from one week before the first muPD-L1 immunization until day 23 to the group 5. The group 4 were feed with chow diet provided by Ssniff for the same time. At day −7, 8, 15, and 23 blood samples from the tail were taken in Sarstedt Micro tubes 1, 1 ml Z gel (cat. no 41.1378.005) before dosing. After 30 min of resting the tubes were centrifuged at 10'000 g for 10 min and stored at −20° C.

ADA Measurement

Nunc Maxisorp flat-bottom 96 well ELISA plates were coated with 100 µl per well of anti muPD-L1 (P1AE4930-001) at 5 µg/mL in NaHCO$_3$ 100 mM buffer overnight at +4° C. The next day the ELISA plates were washed 3 times with PBS+0.05% Tween. For blocking, 100 µl of PBS+2% BSA were added to each well and the ELISA plates were incubated 2 hours at room temperature. The sera were diluted 1 to 50 in PBS+1% FBS in the first raw of round bottom dilution plate, following by a 1 to 3 serial dilution step, 7 times in PBS+1% FBS. The ELISA plates were washed 3 times with PBS+0.05% Tween and 100 µl of the diluted sera were transferred from the dilution plate to the ELISA plate. After 2 hours of incubation at room temperature, the ELISA plates were washed 3 times with PBS+0.05% Tween. For detection of ADAs, 100 µl per well of goat anti mouse IgG Alkaline Phosphatase conjugated (Jackson Cat no 115-055-071) diluted 1:2000 in PBS+1% BSA were added. After 1 hour of incubation at room temperature, the ELISA plates were washed 3 times with PBS+0.05% Tween. 100 µl of substrate P-nitrophenyl phosphate ready to use (Life Technologies, Cat no 002212) were added per well and after 10 min incubation at room temperature, the OD at 405 nm was read as an end-point measurement with a Versamax ELISA reader.

Figure 9:
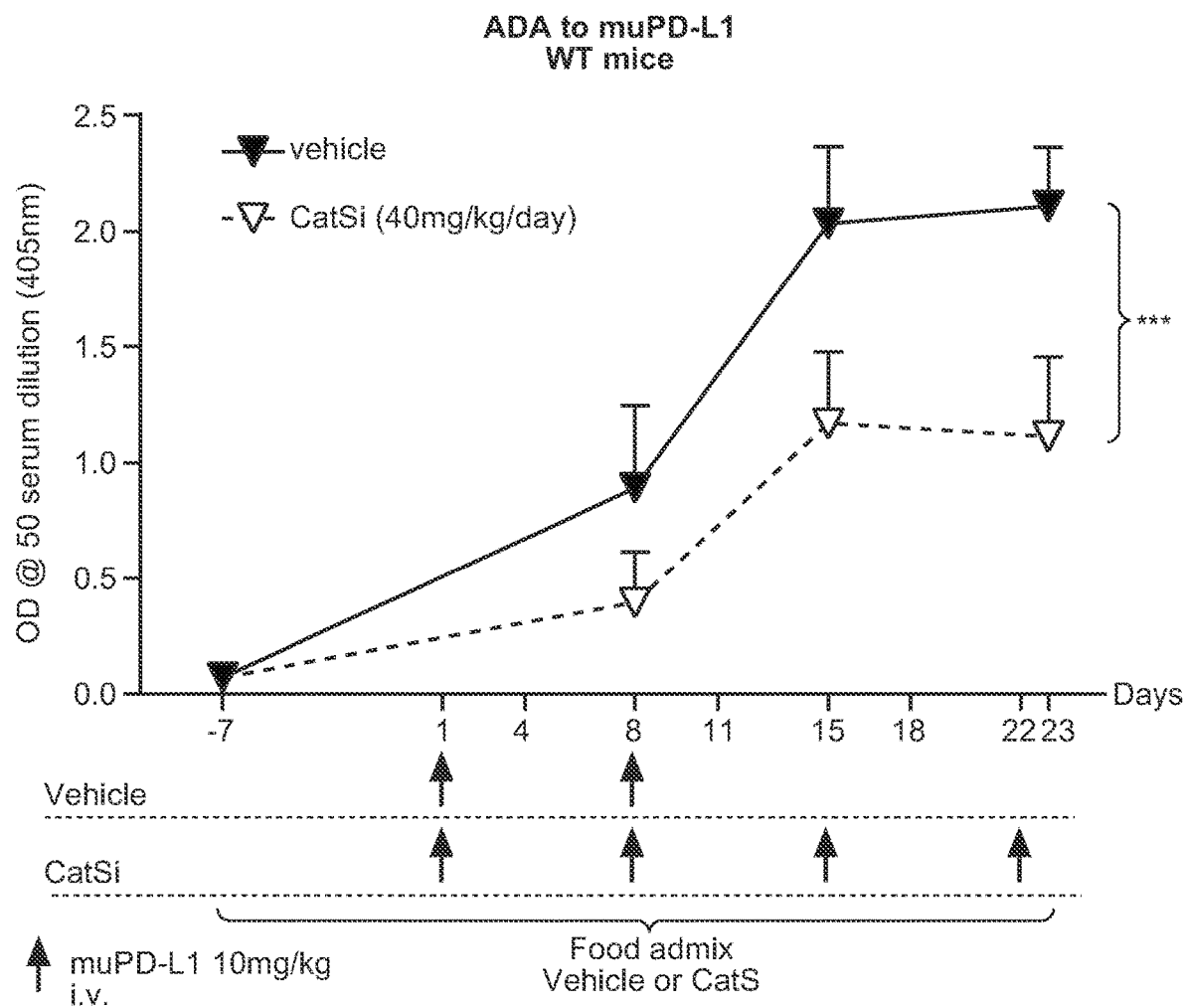

The results are shown in FIG. 9.

Example 8: Mitigation of ADA Against CEA-TCB

Immunization 11-15-week-old mice C57BL/6-Tg (hIgG1,k,l) mixed gender (n=20) were purchased from Taconic (Denmark) and housed at the animal facilities in room with air-conditioned under a 12 hours light/dark cycle in macrolon boxes with enriched environment and free access to water and food. 7×10 µg of CEA-TCB (P1AE3536, huCEA binder CH1A1A/mouse CD3 binder 2C11) were injected at day 0, 4, 7, 11, 14, 18 and 21 subcutaneously in the right flank or the left flank alternatively. The dosage of (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide consumption was 40 mg/kg/day. (2S,4R)-4-[4-(1-methyl-1H-pyrazol-4-yl)-2-trifluoromethyl-benzenesulfonyl]-1-(1-trifluoromethyl-cyclopropanecarbonyl)-pyrrolidine-2-carboxylic acid (1-cyano-cyclopropyl)-amide was given via food admix (Ssniff Spezialdiäten, Germany) daily from one week before the first CEA-TCB immunization until day 28 to the group 2 (n=10). The group 1 (n=10) were feed with chow diet provided by Ssniff for the same time. At day −7, 8, 15, and 28 blood samples from the tail were taken in Sarstedt Micro tubes 1, 1 ml Z gel (cat. no 41.1378.005) before dosing. After 30 min of resting the tubes were centrifuged at 10'000 g for 10 min and stored at −20° C.

ADA Measurement

Nunc Maxisorp flat-bottom 96 well ELISA plates were coated with 100 µl per well of huCEA IgG PGLALA (P1AD9477) or hu anti mouse CD3 (P1AE2779-001-01) respectively at 5 µg/mL in NaHCO$_3$ 100 mM buffer overnight at +4° C. The next day the ELISA plates were washed 3 times with PBS+0.05% Tween. For blocking, 100 µl of PBS+2% BSA were added to each well and the ELISA plates were incubated 2 hours at room temperature. The sera were diluted 1 to 50 in PBS+1% FBS in the first raw of round bottom dilution plate, following by a 1 to 3 serial dilution step, 7 times in PBS+1% FBS. The ELISA plates were washed 3 times with PBS+0.05% Tween and 100 µl of the diluted sera were transferred from the dilution plate to the ELISA plate. After 2 hours of incubation at room temperature, the ELISA plates were washed 3 times with PBS+0.05% Tween. For detection of ADA against CEA, 100 µl per well of goat anti mouse IgG Alkaline Phosphatase conjugated (Jackson Cat no 115-055-071) diluted 1:2000 in PBS+1% BSA were added. For detection of ADA against CD3 binder, 100 µl per well of goat anti mouse IgG2c Alkaline Phosphatase conjugated (Jackson Cat no 115-055-208) diluted 1:2000 in PBS+1% BSA were added. After 1 hour of incubation at room temperature, the ELISA plates were washed 3 times with PBS+0.05% Tween. 100 µl of substrate P-nitrophenyl phosphate ready to use (Life Technologies, Cat no 002212) were added per well and after 10 min incubation at room temperature, the OD at 405 nm was read as an end-point measurement with a Versamax ELISA reader.

Figure 10A:
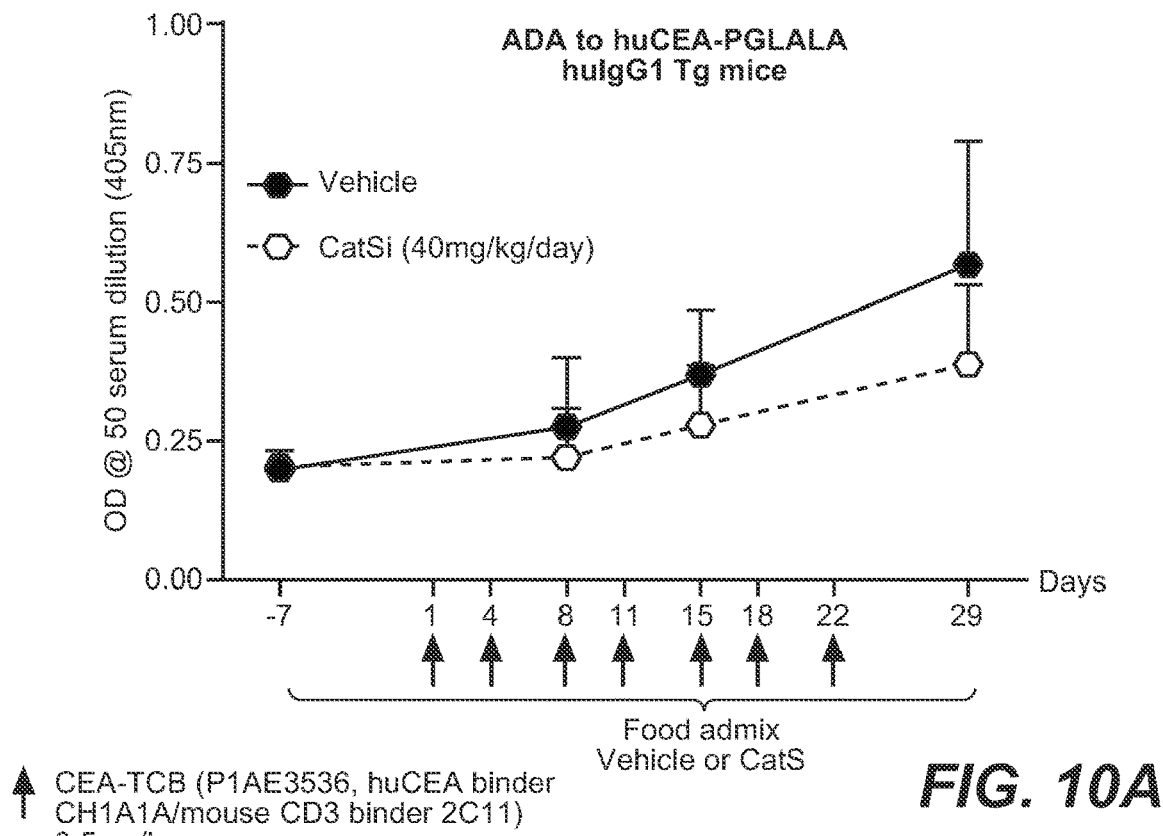
Figure 10B:
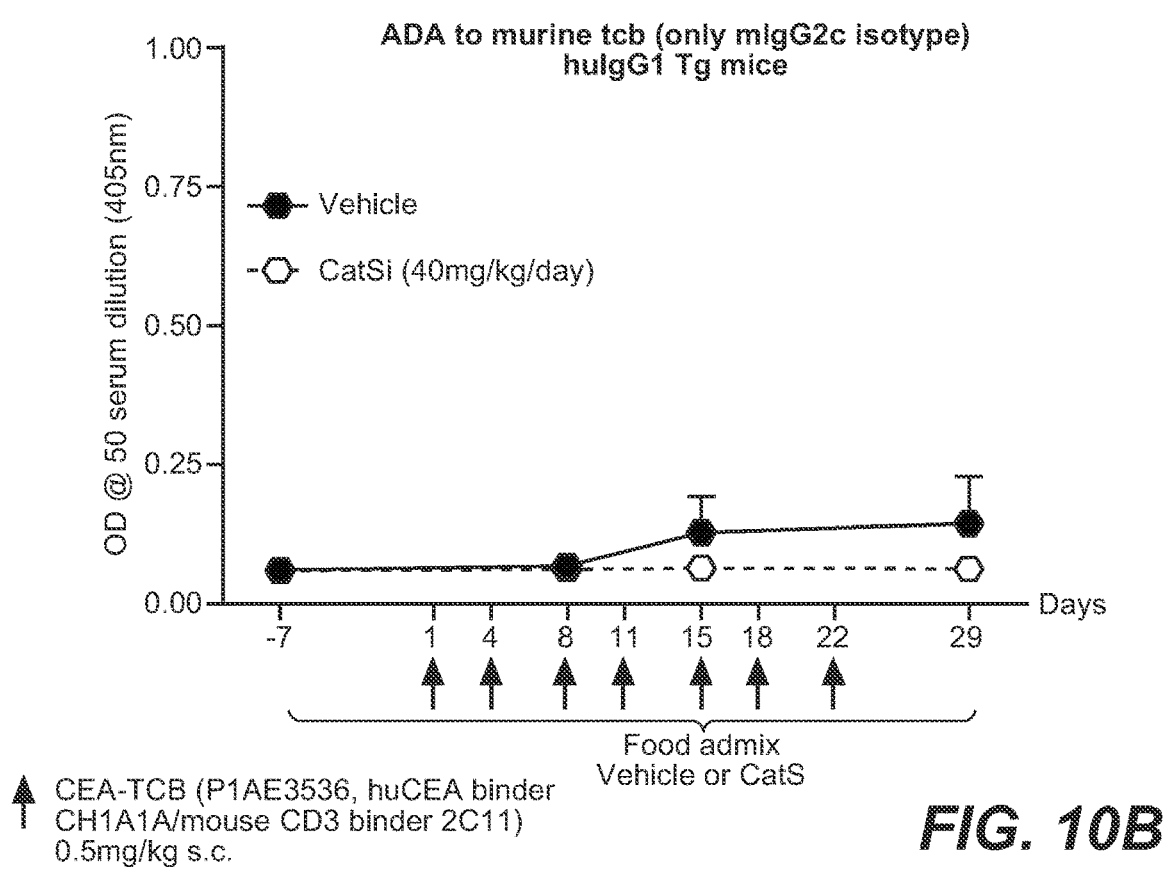

The results are shown in FIGS. 10A and 10B.

What is claimed is:

1. A method for reducing or preventing the formation of anti-drug antibodies (ADA) against a biologic in a subject receiving a treatment with said biologic comprising administering a cathepsin S inhibitor to said subject, wherein the cathepsin S inhibitor is administered to the subject in an amount that is sufficient to reduce or prevent the formation of ADA against the biologic in said subject, wherein the cathepsin S inhibitor is (2S,4R)-4-[4-(1-methyl-1H-pyrazol-4-yl)-2-trifluoromethyl-benzenesulfonyl]-1-(1-triflurom-ethyl-cyclopropanecarbonyl)-pyrrolidine-2-carboxylic acid (1-cyano-cyclopropyl)-amide; or
   (2S, 4R)-4-[4-(5-methyl-tetrazol-2-yl)-2-trifluoromethyl-benzenesulfonyl]-1-(1-trifluromethyl-cyclopropan-ecarbonyl)-pyrrolidine-2-carboxyilic acid (1-cyano-cyclopropyl)-amide;
   or a pharmaceutically acceptable salt thereof.

2. The method of claim 1, wherein the biologic induces, enhances or suppresses an immune response.

3. The method of claim 1, wherein the biologic does not rely on MHC-II antigen presentation.

4. The method of claim 1, wherein the biologic is selected from a protein, a polypeptide, an antibody, a monoclonal antibody, a bispecific antibody, a T-cell bispecific antibody, an antibody fragment, an antibody-drug conjugate, a BiTE, a cytokine and a gene therapy vector.

5. The method of claim 4, wherein the biologic is an antibody.

6. The method of claim 5, wherein the biologic is a monoclonal antibody selected from alemtuzumab, atezolizumab, bevacizumab, cetuximab, panitumumab, pertuzumab, trastuzumab, tositumomab, abciximab, adalimumab, apolizumab, aselizumab, atlizumab, bapineuzumab, basiliximab, bavituximab, belimumab briankinumab, canakinumab, cedelizumab, certolizumab pegol, cidfusituzumab, cidtuzumab, cixutumumab, clazakizumab, crenezumab, daclizumab, dalotuzumab, denosumab, eculizumab, efalizumab, emicizumab, epratuzumab, erlizumab, felvizumab, fontolizumab, golimumab, ipilimumab, imgatuzumab, infliximab, labetuzumab, lebrikizumab, lexatumumab, lintuzumab, lucatumumab, lulizumab pegol, lumretuzumab, mapatumumab, matuzumab, mepolizumab, mogamulizumab, motavizumab, motovizumab, muronomab, natalizumab, necitumumab, nimotuzumab, nolovizumab, numavizumab, obinutuzumab, ocrelizumab, olokizumab, omalizumab, onartuzumab, palivizumab, pascolizumab, pecfusituzumab, pectuzumab, pegylated interferon, pembrolizumab, pexelizumab, priliximab, ralivizumab, ranibizumab, reslivizumab, reslizumab, resyvizumab, rituximab, robatumumab, rontalizumab, rovelizumab, ruplizumab, sarilumab, secukinumab, seribantumab, sifalimumab, sibrotuzumab, siltuximab siplizumab, sontuzumab, tadocizumab, talizumab, tefibazumab, tocilizumab, toralizumab, trastuzumab emtansine, tucusituzumab, umavizumab, urtoxazumab, ustekinumab, vedolizumab, visilizumab, zanolimumab and zalutumumab.

7. The method of claim 1, wherein the biologic is a recombinant fusion protein comprised of a human monoclonal antibody directed against fibroblast activation protein-alpha (FAP) linked to an engineered variant form of interleukin-2 (IL-2v).

8. The method of claim 1, wherein the biologic is cergutuzumab amunaleukin.

9. The method of claim 1, wherein the biologic is an anti-TNFalpha antibody.

10. The method of claim 1, wherein the biologic is infliximab or adalimumab.

11. The method of claim 1, wherein the ADA are produced through a T-cell dependent immune response.

12. The method of claim 1, wherein the ADA are produced through a T-helper cell dependent immune response.

13. The method of claim 1, wherein the ADA are produced by a MHC-II dependent immune response.

14. The method of claim 1, wherein the cathepsin S inhibitor is administered at a dose of between 50 mg/kg/day and 400 mg/kg/day.

15. The method of claim 1, wherein the cathepsin S inhibitor is administered at a dose of between 75 mg/kg/day and 250 mg/kg/day.

16. The method of claim 1, wherein the cathepsin S inhibitor is administered at a dose of 100 mg/kg/day or 200 mg/kg/day.

17. The method of claim 1, wherein the cathepsin S inhibitor is administered at a dose of 100 mg/kg b.i.d.

18. The method of claim 1, wherein the first dose of the cathepsin S inhibitor is administered to the subject before the first dose of the biologic.

19. The method of claim 18, wherein the first dose of the cathepsin S inhibitor is administered to the subject between at least 1 day and 2 weeks before the first dose of the biologic is administered.

20. The method of claim 19, wherein the first dose of the cathepsin S inhibitor is administered to the subject between at least 1 day and 1 week before the first dose of the biologic is administered.

21. The method of claim 20, wherein the first dose of the cathepsin S inhibitor is administered to the subject 1 week before the first dose of the biologic is administered.

22. The method of claim 18, wherein administration to the subject of the cathepsin S inhibitor is continued after the first dose of the cathepsin S inhibitor is administered to the subject and at least until the first dose of the biologic is administered to the subject.

23. The method of claim 18, wherein the cathepsin S inhibitor and/or the biologic is continually administered to the subject after administering to the subject the first effective dose of the cathepsin S inhibitor and the first effective dose of the biologic.

* * * * *